(12) United States Patent
Coonahan et al.

(10) Patent No.: US 10,368,849 B2
(45) Date of Patent: Aug. 6, 2019

(54) SINGLE-INSERTION, MULTIPLE SAMPLING BIOPSY DEVICE USABLE WITH VARIOUS TRANSPORT SYSTEMS AND INTEGRATED MARKERS

(71) Applicant: C. R. Bard, Inc., Tempe, AZ (US)

(72) Inventors: Timothy J. Coonahan, Sterling, MA (US); Stanley O. Thompson, New Boston, NH (US); Jon Taylor, Groton, MA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 568 days.

(21) Appl. No.: 14/625,996

(22) Filed: Feb. 19, 2015

(65) Prior Publication Data

US 2015/0223787 A1   Aug. 13, 2015

Related U.S. Application Data

(60) Continuation of application No. 13/608,609, filed on Sep. 10, 2012, now Pat. No. 8,961,430, which is a division of application No. 11/997,404, filed as application No. PCT/US2006/031326 on Aug. 10, 2006, now Pat. No. 8,282,574.
(Continued)

(51) Int. Cl.
*A61B 10/02* (2006.01)
*A61B 90/00* (2016.01)

(52) U.S. Cl.
CPC ...... *A61B 10/0283* (2013.01); *A61B 10/0275* (2013.01); *A61B 2010/0208* (2013.01); *A61B 2010/0225* (2013.01); *A61B 2090/3987* (2016.02)

(58) Field of Classification Search
CPC .......................................... A61B 10/02–0283
See application file for complete search history.

(56) References Cited

U.S. PATENT DOCUMENTS 737,293 A    8/1903  Summerfeldt
1,585,934 A    5/1926  Muir
(Continued)

FOREIGN PATENT DOCUMENTS

CN    101011268 A    8/2007
CN    101032420 A    9/2007
(Continued)

*Primary Examiner* — Devin B Henson
*Assistant Examiner* — H. Q. Nguyen

(57) ABSTRACT

A biopsy device includes a biopsy sample extraction needle having a sample extraction end, a recovery end, and a transport channel linking the extraction and recovery ends. In a first configuration, a valve has a first position wherein the valve directly connects a pump to an ambient vent and the pump can reduce the pressure in at least the sample extraction end. In a second configuration, the valve has a second position wherein the valve directly connects the pump to a fluid reservoir and the pump can draw fluid from the fluid reservoir. In a third configuration, the valve has a third position wherein the valve directly connects the pump to the extraction end and the pump can supply fluid to the extraction end to flush fluid along the transport channel from the extraction end to the recovery end to transport a sample along the transport channel.

15 Claims, 13 Drawing Sheets

Related U.S. Application Data

(60) Provisional application No. 60/707,228, filed on Aug. 10, 2005.

(56) References Cited

U.S. PATENT DOCUMENTS

| | | | |
|---|---|---|---|
| 1,663,761 A | 3/1928 | Johnson |
| 2,953,934 A | 9/1960 | Sundt |
| 3,019,733 A | 2/1962 | Braid |
| 3,224,434 A | 12/1965 | Molomut et al. |
| 3,289,669 A | 12/1966 | Dwyer et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |
| 3,785,380 A | 1/1974 | Brumfield |
| 3,800,783 A | 4/1974 | Jamshidi |
| 3,844,272 A | 10/1974 | Banko |
| 3,882,849 A | 5/1975 | Jamshidi |
| 3,889,682 A | 6/1975 | Denis et al. |
| 3,916,948 A | 11/1975 | Benjamin |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,393,879 A | 7/1983 | Milgrom |
| 4,445,509 A | 5/1984 | Auth |
| 4,490,137 A | 12/1984 | Moukheibir |
| 4,549,554 A | 10/1985 | Markham |
| 4,577,629 A | 3/1986 | Martinez |
| 4,589,414 A | 5/1986 | Yoshida et al. |
| 4,603,694 A | 8/1986 | Wheeler |
| 4,605,011 A | 8/1986 | Naslund |
| 4,616,215 A | 10/1986 | Maddalena |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,678,459 A | 7/1987 | Onik et al. |
| 4,696,298 A | 9/1987 | Higgins et al. |
| 4,702,260 A | 10/1987 | Wang |
| 4,706,687 A | 11/1987 | Rogers |
| 4,776,346 A | 10/1988 | Beraha et al. |
| 4,792,327 A | 12/1988 | Swartz |
| 4,832,044 A | 5/1989 | Garg |
| 4,844,064 A | 7/1989 | Thimsen et al. |
| 4,844,087 A | 7/1989 | Garg |
| 4,850,354 A | 7/1989 | McGurk-Burleson et al. |
| 4,893,635 A | 1/1990 | de Groot et al. |
| 4,907,598 A | 3/1990 | Bauer |
| RE33,258 E | 7/1990 | Onik et al. |
| 4,940,061 A | 7/1990 | Terwilliger et al. |
| 4,952,817 A | 8/1990 | Bolan et al. |
| 4,958,625 A | 9/1990 | Bates et al. |
| 4,967,762 A | 11/1990 | Devries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,048,538 A | 9/1991 | Terwilliger et al. |
| 5,057,822 A | 10/1991 | Hoffman |
| 5,078,603 A | 1/1992 | Cohen |
| 5,125,413 A | 6/1992 | Baran |
| 5,138,245 A | 8/1992 | Mattinger et al. |
| 5,146,921 A | 9/1992 | Terwilliger et al. |
| 5,156,160 A | 10/1992 | Bennett |
| 5,158,528 A | 10/1992 | Walker et al. |
| 5,172,702 A | 12/1992 | Leigh et al. |
| 5,176,628 A | 1/1993 | Charles et al. |
| 5,183,052 A | 2/1993 | Terwilliger |
| 5,197,484 A | 3/1993 | Kornberg et al. |
| 5,211,627 A | 5/1993 | William |
| 5,223,012 A | 6/1993 | Best et al. |
| 5,225,763 A | 7/1993 | Krohn et al. |
| 5,234,000 A | 8/1993 | Hakky et al. |
| 5,236,334 A | 8/1993 | Bennett |
| 5,242,404 A | 9/1993 | Conley et al. |
| 5,249,583 A | 10/1993 | Mallaby |
| 5,254,117 A | 10/1993 | Rigby et al. |
| 5,282,476 A | 2/1994 | Terwilliger |
| 5,282,477 A | 2/1994 | Bauer |
| 5,290,253 A | 3/1994 | Kira |
| 5,305,762 A * | 4/1994 | Acorn ................ A61M 16/208 |
| | | | 600/529 |
| 5,324,306 A | 6/1994 | Makower et al. |
| 5,334,183 A | 8/1994 | Wuchinich |
| 5,335,671 A | 8/1994 | Clement |
| 5,368,029 A | 11/1994 | Holcombe et al. |
| 5,368,045 A | 11/1994 | Clement et al. |
| 5,383,874 A | 1/1995 | Jackson et al. |
| 5,397,462 A | 3/1995 | Higashijima et al. |
| 5,400,798 A | 3/1995 | Baran |
| 5,439,474 A | 8/1995 | Li |
| 5,458,112 A | 10/1995 | Weaver |
| 5,469,860 A | 11/1995 | De Santis |
| 5,471,994 A | 12/1995 | Guirguis |
| 5,479,486 A | 12/1995 | Saji |
| 5,485,917 A | 1/1996 | Early |
| 5,492,130 A | 2/1996 | Chiou |
| 5,511,556 A | 4/1996 | DeSantis |
| 5,526,822 A | 6/1996 | Burbank et al. |
| 5,535,755 A | 7/1996 | Heske |
| 5,546,957 A | 8/1996 | Heske |
| 5,554,151 A | 9/1996 | Hinchliffe |
| 5,560,373 A | 10/1996 | De Santis |
| 5,564,436 A | 10/1996 | Hakky et al. |
| 5,569,284 A | 10/1996 | Young et al. |
| 5,575,293 A | 11/1996 | Miller et al. |
| 5,591,170 A | 1/1997 | Spievack et al. |
| 5,601,583 A | 2/1997 | Donahue et al. |
| 5,601,585 A | 2/1997 | Banik et al. |
| 5,602,449 A | 2/1997 | Krause et al. |
| 5,612,738 A | 3/1997 | Kim |
| 5,617,874 A | 4/1997 | Baran |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey et al. |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,779,649 A | 7/1998 | Herbert |
| 5,788,651 A | 8/1998 | Weilandt |
| 5,792,167 A | 8/1998 | Kablik et al. |
| 5,807,282 A | 9/1998 | Fowler |
| 5,817,033 A | 10/1998 | DeSantis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,871,699 A | 2/1999 | Ruggeri |
| 5,879,365 A | 3/1999 | Whitfield et al. |
| 5,908,233 A | 6/1999 | Heskett et al. |
| 5,913,857 A | 6/1999 | Ritchart et al. |
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregoire et al. |
| 5,951,490 A | 9/1999 | Fowler |
| 5,951,575 A | 9/1999 | Bolduc et al. |

(56) References Cited

U.S. PATENT DOCUMENTS

| | | |
|---|---|---|
| 5,964,716 A | 10/1999 | Gregoire et al. |
| 5,971,939 A | 10/1999 | DeSantis et al. |
| 5,976,164 A | 11/1999 | Bencini et al. |
| 5,980,469 A | 11/1999 | Burbank et al. |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,032,673 A * | 3/2000 | Savage ............... A61B 18/1485 128/898 |
| 6,036,657 A | 3/2000 | Milliman et al. |
| 6,050,955 A | 4/2000 | Bryan et al. |
| 6,055,870 A | 5/2000 | Jaeger |
| 6,071,247 A | 6/2000 | Kennedy |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,434,507 B1 | 8/2002 | Clayton et al. |
| 6,436,054 B1 | 8/2002 | Viola et al. |
| 6,461,302 B1 | 10/2002 | Thompson |
| 6,471,659 B2 | 10/2002 | Eggers et al. |
| 6,482,158 B2 | 11/2002 | Mault |
| 6,485,436 B1 | 11/2002 | Truckai et al. |
| 6,488,636 B2 | 12/2002 | Bryan et al. |
| 6,494,844 B1 | 12/2002 | Van Bladel et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,544,194 B1 | 4/2003 | Kortenbach et al. |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1 | 7/2003 | Smith et al. |
| 6,586,585 B1 | 7/2003 | Bastian |
| 6,592,530 B1 | 7/2003 | Farhadi |
| 6,626,849 B2 | 9/2003 | Huitema et al. |
| 6,632,182 B1 | 10/2003 | Treat |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,702,832 B2 | 3/2004 | Ross et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,755,802 B2 | 6/2004 | Bell |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,850,159 B1 | 2/2005 | Mudge |
| 6,860,860 B2 | 3/2005 | Viola |
| 6,875,183 B2 | 4/2005 | Cervi |
| 6,887,210 B2 | 5/2005 | Quay |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Homer et al. |
| 7,004,174 B2 | 2/2006 | Eggers et al. |
| 7,010,332 B1 | 3/2006 | Irvin et al. |
| 7,025,732 B2 | 4/2006 | Thompson et al. |
| D525,583 S | 7/2006 | Vu |
| 7,108,660 B2 | 9/2006 | Stephens et al. |
| 7,153,274 B2 | 12/2006 | Stephens et al. |
| 7,156,814 B1 | 1/2007 | Williamson, IV et al. |
| 7,182,754 B2 | 2/2007 | Brigham et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,252,641 B2 | 8/2007 | Thompson et al. |
| 7,276,032 B2 | 10/2007 | Hibner |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,390,306 B2 | 6/2008 | Mark |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,419,472 B2 | 9/2008 | Hibner et al. |
| 7,432,813 B2 | 10/2008 | Postma |
| 7,452,367 B2 | 11/2008 | Rassman et al. |
| 7,458,940 B2 | 12/2008 | Miller |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,491,177 B2 | 2/2009 | Hibner |
| 7,494,473 B2 | 2/2009 | Eggers et al. |
| 7,497,833 B2 | 3/2009 | Miller |
| 7,510,534 B2 | 3/2009 | Burdorff et al. |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,549,978 B2 | 6/2009 | Carlson et al. |
| 7,575,557 B2 | 8/2009 | Morton et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,758,515 B2 | 7/2010 | Hibner |
| 7,762,961 B2 | 7/2010 | Heske et al. |
| 7,806,834 B2 | 10/2010 | Beckman et al. |
| 7,828,746 B2 | 11/2010 | Teague |
| 7,828,747 B2 | 11/2010 | Heske et al. |
| 7,841,991 B2 | 11/2010 | Douglas et al. |
| 7,854,706 B2 | 12/2010 | Hibner |
| 7,862,517 B2 | 1/2011 | Tsonton et al. |
| 7,871,384 B2 | 1/2011 | Thompson et al. |

(56) References Cited

U.S. PATENT DOCUMENTS

| | | |
|---|---|---|
| 7,883,476 B2 | 2/2011 | Miller et al. |
| 7,883,494 B2 | 2/2011 | Martin |
| 7,906,076 B2 | 3/2011 | Fischer |
| 7,914,462 B2 | 3/2011 | Hutchins et al. |
| 7,959,580 B2 | 6/2011 | Mccullough et al. |
| 7,974,681 B2 | 7/2011 | Wallace et al. |
| 8,002,713 B2 | 8/2011 | Heske et al. |
| 8,012,102 B2 | 9/2011 | McCullough et al. |
| 8,016,772 B2 | 9/2011 | Heske et al. |
| 8,016,844 B2 | 9/2011 | Privitera et al. |
| 8,052,614 B2 | 11/2011 | Heske et al. |
| 8,052,615 B2 | 11/2011 | Reuber et al. |
| 8,057,402 B2 | 11/2011 | Hibner et al. |
| 8,073,008 B2 | 12/2011 | Mehta et al. |
| 8,075,495 B2 | 12/2011 | Andreyko et al. |
| 8,083,671 B2 | 12/2011 | Boulais et al. |
| 8,109,885 B2 | 2/2012 | Heske et al. |
| 8,118,755 B2 | 2/2012 | Hibner et al. |
| 8,152,738 B2 | 4/2012 | Li et al. |
| 8,157,744 B2 | 4/2012 | Jorgensen et al. |
| 8,162,851 B2 | 4/2012 | Heske et al. |
| 8,172,771 B2 | 5/2012 | Miller et al. |
| 8,172,773 B2 | 5/2012 | Heske et al. |
| 8,187,204 B2 | 5/2012 | Miller et al. |
| 8,190,238 B2 | 5/2012 | Moll et al. |
| 8,206,409 B2 | 6/2012 | Privitera et al. |
| 8,251,916 B2 | 8/2012 | Speeg et al. |
| 8,251,917 B2 | 8/2012 | Almazan |
| 8,262,585 B2 | 9/2012 | Thompson et al. |
| 8,262,586 B2 | 9/2012 | Anderson et al. |
| 8,267,868 B2 | 9/2012 | Taylor et al. |
| 8,277,393 B2 | 10/2012 | Miller et al. |
| 8,283,890 B2 | 10/2012 | Videbaek |
| 8,313,444 B2 | 11/2012 | Thompson et al. |
| 8,343,069 B2 | 1/2013 | Uchiyama et al. |
| 8,366,636 B2 | 2/2013 | Videbaek |
| 8,430,824 B2 | 4/2013 | Videbaek et al. |
| 8,430,827 B2 | 4/2013 | Nicoson et al. |
| 8,485,987 B2 | 7/2013 | Videbaek et al. |
| 8,485,989 B2 | 7/2013 | Videbaek |
| 8,597,205 B2 | 12/2013 | Seiger et al. |
| 8,597,206 B2 | 12/2013 | Videback |
| 8,702,621 B2 | 4/2014 | Mccullough et al. |
| 8,702,622 B2 | 4/2014 | McCullough et al. |
| 8,721,563 B2 | 5/2014 | Taylor et al. |
| 8,728,003 B2 | 5/2014 | Taylor et al. |
| 8,728,004 B2 | 5/2014 | Heske et al. |
| 8,771,200 B2 | 7/2014 | Thompson et al. |
| 8,864,680 B2 | 10/2014 | Videbæk et al. |
| 8,926,527 B2 | 1/2015 | Jorgensen et al. |
| 8,956,306 B2 | 2/2015 | Hibner |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0000403 A1 | 1/2002 | Tanaka et al. |
| 2002/0029007 A1 | 3/2002 | Bryan et al. |
| 2002/0065474 A1 | 5/2002 | Viola |
| 2002/0067151 A1 | 6/2002 | Tanishita |
| 2002/0068878 A1 | 6/2002 | Jasonni et al. |
| 2002/0082518 A1 | 6/2002 | Weiss et al. |
| 2002/0107043 A1 | 8/2002 | Adamson et al. |
| 2002/0115942 A1 | 8/2002 | Stanford et al. |
| 2002/0120212 A1 | 8/2002 | Ritchart et al. |
| 2002/0143269 A1 | 10/2002 | Neuenfeldt |
| 2002/0156395 A1 | 10/2002 | Stephens et al. |
| 2003/0023188 A1 | 1/2003 | Kritzman et al. |
| 2003/0023239 A1 | 1/2003 | Burbank et al. |
| 2003/0073929 A1 | 4/2003 | Baltschun et al. |
| 2003/0093103 A1 | 5/2003 | Malackowski et al. |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0034280 A1 | 2/2004 | Privitera et al. |
| 2004/0049128 A1 | 3/2004 | Miller et al. |
| 2004/0054299 A1 | 3/2004 | Burdorff et al. |
| 2004/0082915 A1 | 4/2004 | Kadan |
| 2004/0092980 A1 | 5/2004 | Cesarini et al. |
| 2004/0092992 A1 | 5/2004 | Adams et al. |
| 2004/0162505 A1 | 8/2004 | Kaplan et al. |
| 2004/0167428 A1 | 8/2004 | Quick et al. |
| 2004/0186393 A1 | 9/2004 | Leigh et al. |
| 2004/0210161 A1 | 10/2004 | Burdorff et al. |
| 2004/0215103 A1 | 10/2004 | Mueller, Jr. et al. |
| 2004/0220495 A1 | 11/2004 | Cahir et al. |
| 2004/0230135 A1 | 11/2004 | Merkle |
| 2004/0230188 A1 | 11/2004 | Cioanta et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0054947 A1 | 3/2005 | Goldenberg |
| 2005/0065453 A1 | 3/2005 | Shabaz et al. |
| 2005/0080355 A1 | 4/2005 | Mark |
| 2005/0085838 A1 | 4/2005 | Thompson et al. |
| 2005/0088120 A1 | 4/2005 | Avis |
| 2005/0101879 A1 | 5/2005 | Shidham et al. |
| 2005/0113715 A1 | 5/2005 | Schwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0165329 A1 | 7/2005 | Taylor et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0275378 A1 | 12/2005 | Canino et al. |
| 2005/0277829 A1 | 12/2005 | Tsonton et al. |
| 2005/0277871 A1 | 12/2005 | Sells |
| 2005/0288605 A1 | 12/2005 | Pellegrino et al. |
| 2006/0030784 A1 | 2/2006 | Miller et al. |
| 2006/0074344 A1 | 4/2006 | Hibner |
| 2006/0074345 A1 | 4/2006 | Hibner |
| 2006/0074350 A1 | 4/2006 | Cash |
| 2006/0113958 A1 | 6/2006 | Lobert et al. |
| 2006/0116603 A1 | 6/2006 | Shibazaki et al. |
| 2006/0122535 A1 | 6/2006 | Daum |
| 2006/0129063 A1 | 6/2006 | Thompson et al. |
| 2006/0149162 A1 | 7/2006 | Daw et al. |
| 2006/0173377 A1 | 8/2006 | McCullough et al. |
| 2006/0178666 A1 | 8/2006 | Cosman et al. |
| 2006/0184063 A1 | 8/2006 | Miller |
| 2006/0200042 A1 | 9/2006 | Weikel, Jr. et al. |
| 2006/0241515 A1 | 10/2006 | Jones et al. |
| 2006/0258956 A1 | 11/2006 | Haberstich et al. |
| 2006/0260994 A1 | 11/2006 | Mark et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0032743 A1 | 2/2007 | Hibner |
| 2007/0055173 A1 | 3/2007 | DeLonzor et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118048 A1 | 5/2007 | Stephens et al. |
| 2007/0118049 A1 | 5/2007 | Viola |
| 2007/0123797 A1 | 5/2007 | Krause |
| 2007/0149893 A1 | 6/2007 | Heske et al. |
| 2007/0149894 A1 | 6/2007 | Heske et al. |

(56) References Cited

U.S. PATENT DOCUMENTS

| | | |
|---|---|---|
| 2007/0161925 A1 | 7/2007 | Quick et al. |
| 2007/0167736 A1 | 7/2007 | Dietz et al. |
| 2007/0167782 A1 | 7/2007 | Callahan et al. |
| 2007/0167828 A1 | 7/2007 | Saadat |
| 2007/0167943 A1 | 7/2007 | Janssen et al. |
| 2007/0179401 A1 | 8/2007 | Hibner |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0292858 A1 | 12/2007 | Chen et al. |
| 2007/0293788 A1 | 12/2007 | Entrekin et al. |
| 2007/0293830 A1 | 12/2007 | Martin |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0071193 A1 | 3/2008 | Reuber et al. |
| 2008/0079391 A1 | 4/2008 | Schroeck et al. |
| 2008/0103411 A1 | 5/2008 | Van Bladel et al. |
| 2008/0110261 A1 | 5/2008 | Randall et al. |
| 2008/0125634 A1 | 5/2008 | Ryan et al. |
| 2008/0135443 A1 | 6/2008 | Frojd et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0214955 A1 | 9/2008 | Speeg et al. |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0287826 A1 | 11/2008 | Videbaek et al. |
| 2008/0306406 A1 | 12/2008 | Thompson et al. |
| 2008/0308607 A1 | 12/2008 | Timm et al. |
| 2008/0319341 A1 | 12/2008 | Taylor et al. |
| 2009/0015208 A1 | 1/2009 | White et al. |
| 2009/0030405 A1 | 1/2009 | Quick et al. |
| 2009/0048532 A1 | 2/2009 | Stephens et al. |
| 2009/0048533 A1 | 2/2009 | Miller |
| 2009/0062624 A1 | 3/2009 | Neville |
| 2009/0082695 A1 | 3/2009 | Whitehead |
| 2009/0087249 A1 | 4/2009 | Flagle et al. |
| 2009/0088666 A1 | 4/2009 | Miller et al. |
| 2009/0112118 A1 | 4/2009 | Quick, Jr. et al. |
| 2009/0125062 A1 | 5/2009 | Arnin |
| 2009/0137927 A1 | 5/2009 | Miller |
| 2009/0146609 A1 | 6/2009 | Santos |
| 2009/0171242 A1 | 7/2009 | Hibner |
| 2009/0171243 A1 | 7/2009 | Hibner et al. |
| 2009/0204022 A1 | 8/2009 | Schwindt |
| 2009/0227893 A1 | 9/2009 | Coonahan et al. |
| 2009/0281453 A1 | 11/2009 | Tsonton et al. |
| 2010/0030020 A1 | 2/2010 | Sanders et al. |
| 2010/0030108 A1 | 2/2010 | Anderson et al. |
| 2010/0063416 A1 | 3/2010 | Cicenas et al. |
| 2010/0106053 A1 | 4/2010 | Videbaek et al. |
| 2010/0152611 A1 | 6/2010 | Parihar et al. |
| 2010/0160820 A1 | 6/2010 | Weikel, Jr. et al. |
| 2010/0210966 A1 | 8/2010 | Videbaek |
| 2010/0222700 A1 | 9/2010 | Hibner |
| 2010/0234760 A1 | 9/2010 | Almazan |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2010/0324449 A1 | 12/2010 | Rostaing et al. |
| 2011/0021946 A1 | 1/2011 | Heske et al. |
| 2011/0152715 A1 | 6/2011 | Delap et al. |
| 2011/0160611 A1 | 6/2011 | Ritchart et al. |
| 2011/0208085 A1 | 8/2011 | Mccullough et al. |
| 2011/0295150 A1 | 12/2011 | Mccullough et al. |
| 2012/0071787 A1 | 3/2012 | Reuber et al. |
| 2012/0095366 A1 | 4/2012 | Heske et al. |
| 2012/0184873 A1 | 7/2012 | Jorgensen et al. |
| 2012/0191009 A1 | 7/2012 | Hoon et al. |
| 2012/0203135 A1 | 8/2012 | Heske et al. |
| 2012/0215130 A1 | 8/2012 | Field et al. |
| 2012/0238905 A1 | 9/2012 | Heske et al. |
| 2012/0310109 A1 | 12/2012 | Almazan |
| 2013/0023789 A1 | 1/2013 | Anderson et al. |
| 2013/0023791 A1 | 1/2013 | Thompson et al. |
| 2013/0289441 A1 | 10/2013 | Videbaek et al. |
| 2014/0228706 A1 | 8/2014 | Mccullough et al. |
| 2014/0371585 A1 | 12/2014 | Thompson et al. |
| 2015/0018712 A1 | 1/2015 | Seiger et al. |
| 2015/0025415 A1 | 1/2015 | Videbaek et al. |
| 2015/0073301 A1 | 3/2015 | Videbaek et al. |
| 2015/0094613 A1 | 4/2015 | Jorgensen et al. |
| 2015/0133814 A1 | 5/2015 | Almazan |
| 2015/0148702 A1 | 5/2015 | Heske et al. |
| 2015/0190124 A1 | 7/2015 | McCullough et al. |
| 2015/0342579 A1 | 12/2015 | Heske et al. |
| 2016/0256138 A1 | 9/2016 | Videbaek et al. |
| 2016/0367229 A1 | 12/2016 | Jorgensen et al. |
| 2016/0367230 A1 | 12/2016 | Almazan |
| 2016/0374650 A1 | 12/2016 | Heske et al. |
| 2017/0042517 A1 | 2/2017 | Heske et al. |
| 2017/0181732 A1 | 6/2017 | Videbaek et al. |
| 2017/0258458 A1 | 9/2017 | Seiger et al. |

FOREIGN PATENT DOCUMENTS

| | | |
|---|---|---|
| DE | 3924291 A1 | 1/1991 |
| DE | 4041614 C1 | 10/1992 |
| DE | 3924291 C2 | 7/2000 |
| DE | 10034297 A1 | 4/2001 |
| DE | 10026303 A1 | 2/2002 |
| DE | 20204363 U1 | 5/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1604615 A1 | 12/2005 |
| EP | 1665989 A2 | 6/2006 |
| EP | 1698282 A1 | 9/2006 |
| EP | 1829487 A1 | 9/2007 |
| EP | 2095772 A1 | 9/2009 |
| EP | 2106750 A2 | 10/2009 |
| EP | 1569561 B1 | 10/2010 |
| FR | 1345429 A | 12/1963 |
| FR | 2739293 A1 | 4/1997 |
| GB | 2018601 A | 10/1979 |
| JP | 1-126957 A | 9/1987 |
| JP | H10508504 A | 8/1998 |

(56) References Cited

FOREIGN PATENT DOCUMENTS

| | | | |
|---|---|---|---|
| JP | 2005530554 | A | 10/2005 |
| JP | 2006509545 | A | 3/2006 |
| JP | 2006528907 | A | 12/2006 |
| JP | 2007502159 | A | 2/2007 |
| WO | 9508945 | A2 | 4/1995 |
| WO | 9624289 | A2 | 8/1996 |
| WO | 9628097 | A1 | 9/1996 |
| WO | 9734531 | A1 | 9/1997 |
| WO | 9825522 | A1 | 6/1998 |
| WO | 9831285 | A1 | 7/1998 |
| WO | 9835615 | A1 | 8/1998 |
| WO | 9846290 | A1 | 10/1998 |
| WO | 9933501 | A1 | 7/1999 |
| WO | 0004832 | A1 | 2/2000 |
| WO | 0030546 | A1 | 6/2000 |
| WO | 0059378 | A2 | 10/2000 |
| WO | 0172230 | A1 | 10/2001 |
| WO | 0222023 | A1 | 3/2002 |
| WO | 0232318 | A1 | 4/2002 |
| WO | 02069808 | A2 | 9/2002 |
| WO | 2005013830 | A1 | 2/2005 |
| WO | 2006005342 | A1 | 1/2006 |
| WO | 2006015302 | A1 | 2/2006 |
| WO | 2007047128 | A1 | 4/2007 |
| WO | 2007095330 | A2 | 8/2007 |
| WO | 2007112751 | A2 | 10/2007 |
| WO | 2008021687 | A1 | 2/2008 |
| WO | 2008024684 | A2 | 2/2008 |
| WO | 2008040812 | A1 | 4/2008 |
| WO | 2008131362 | A2 | 10/2008 |

\* cited by examiner

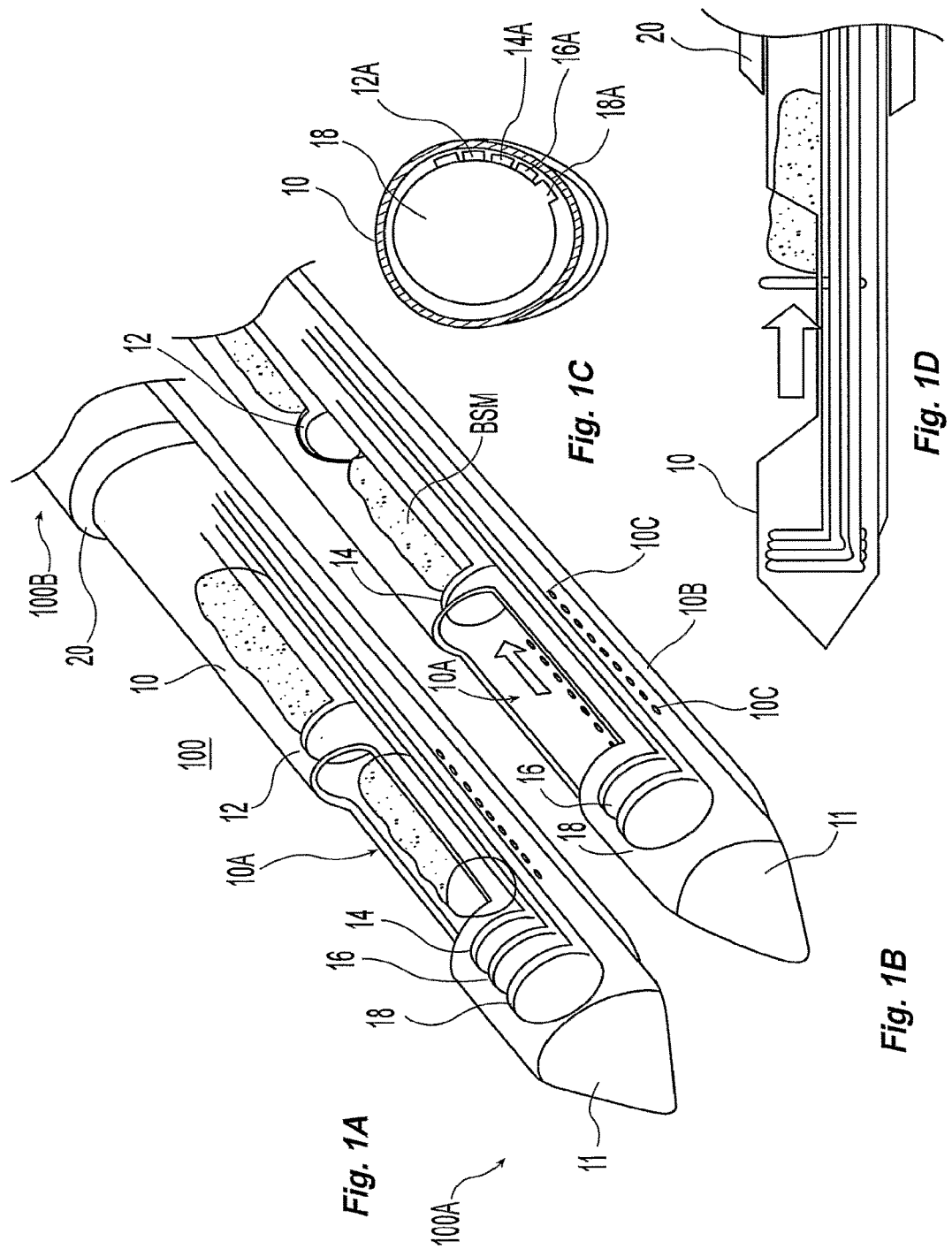

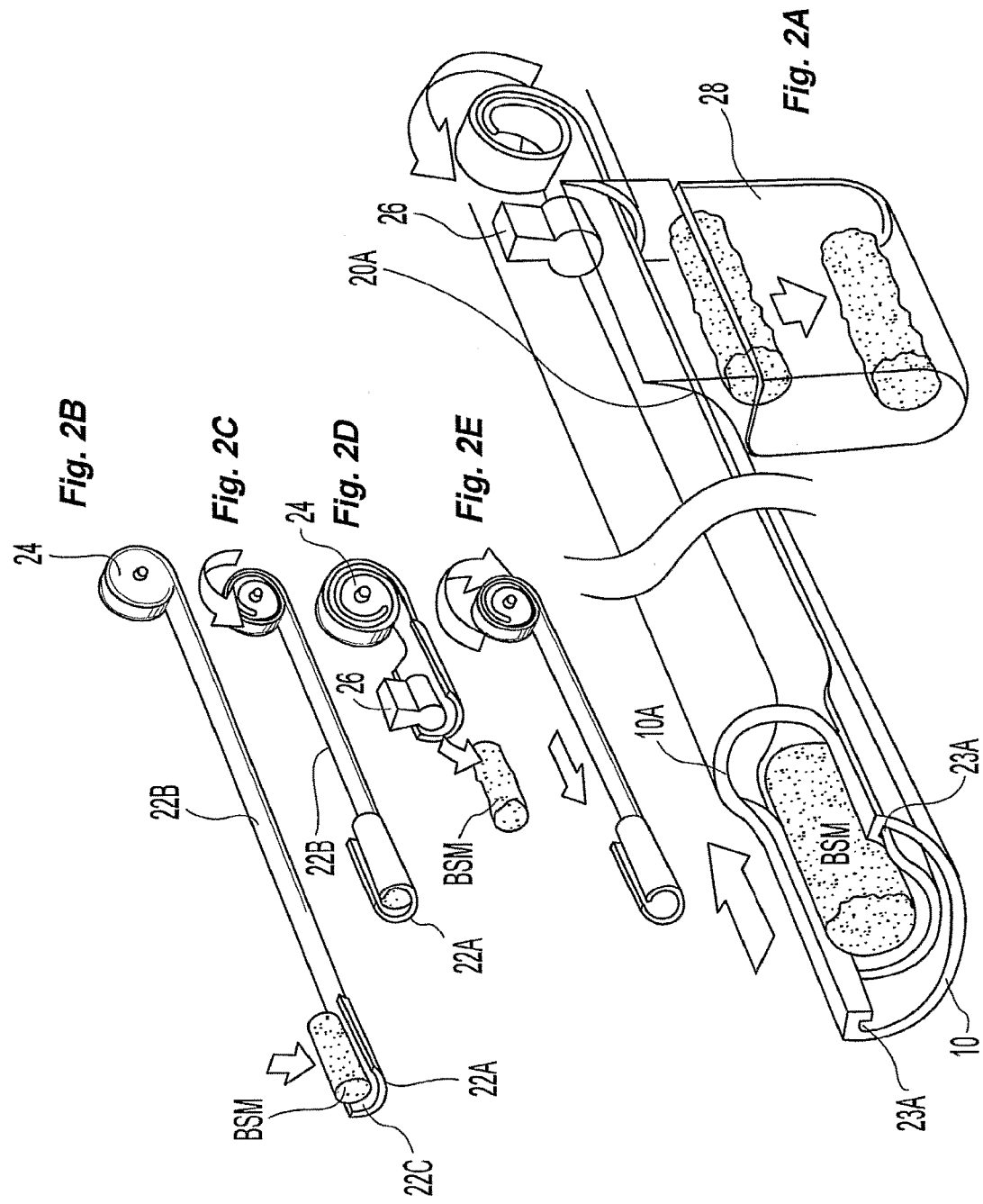

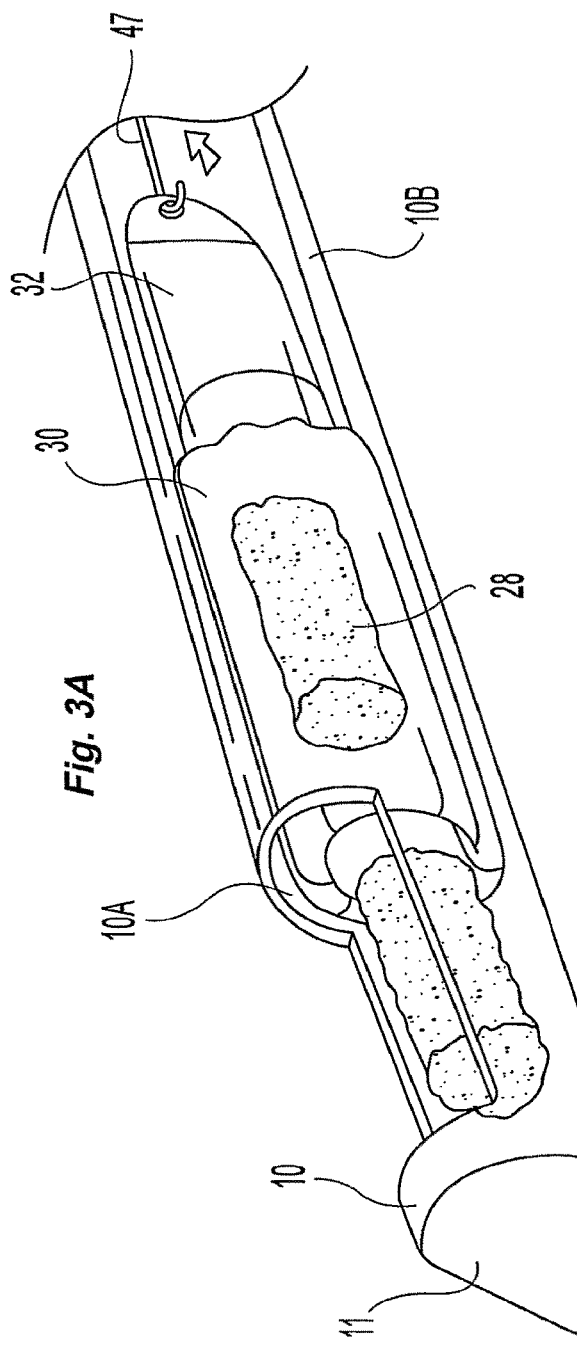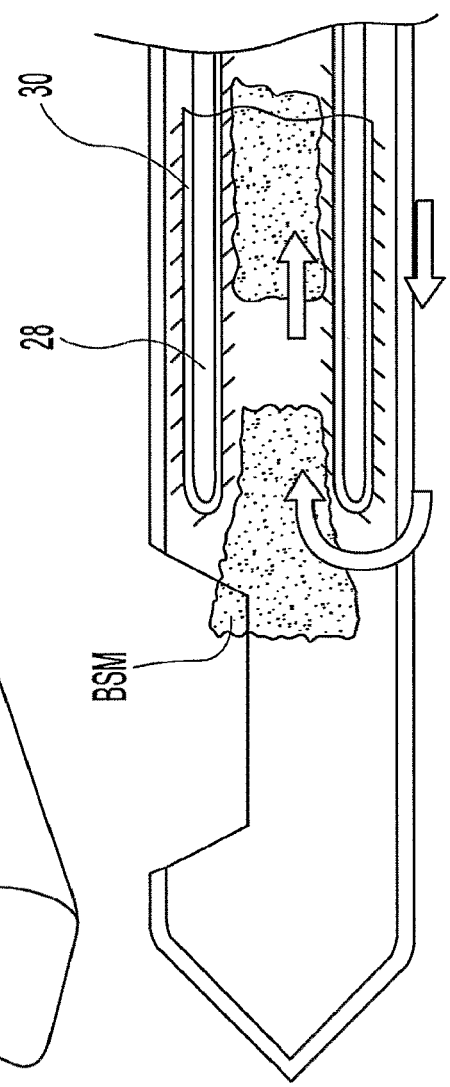

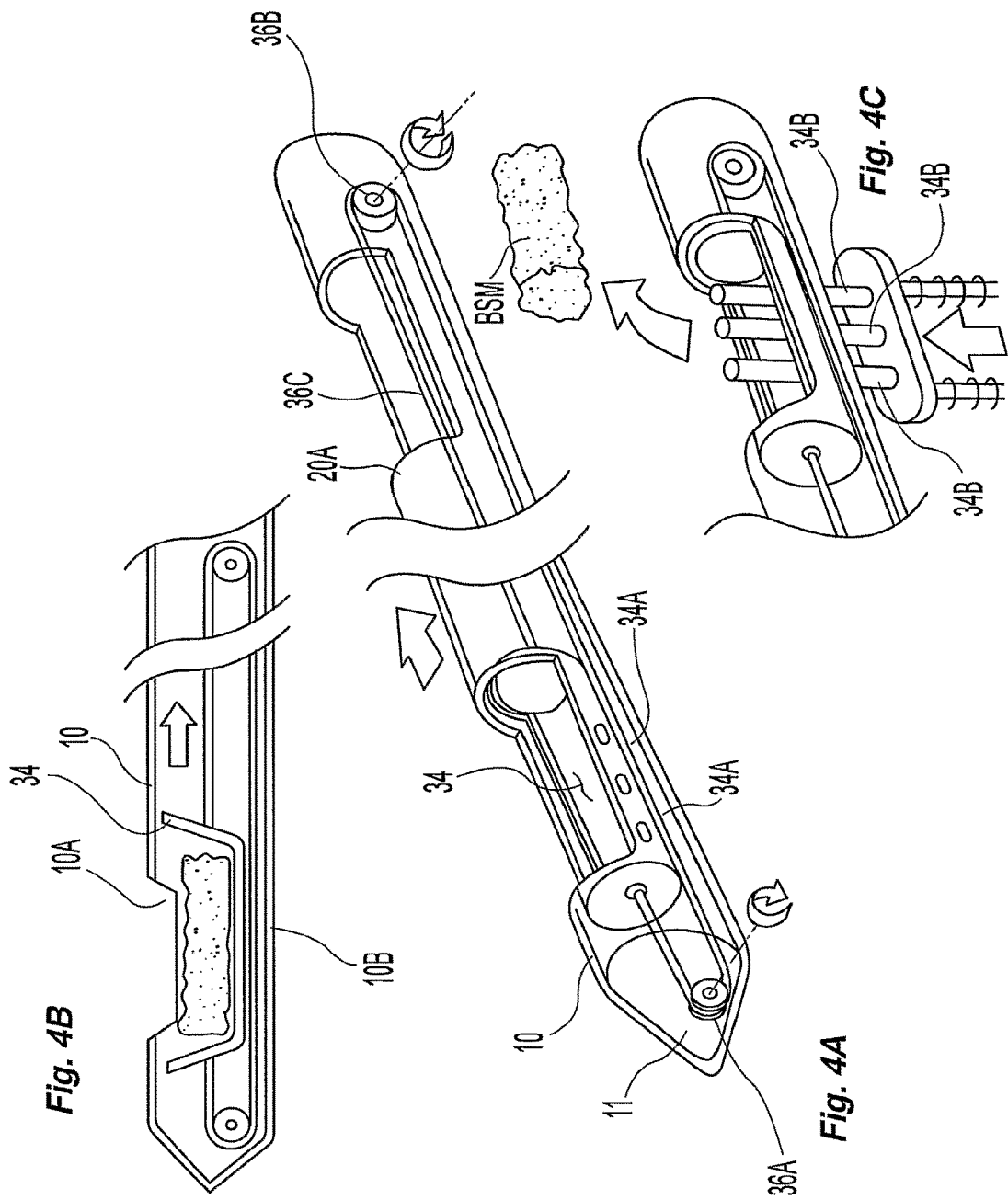

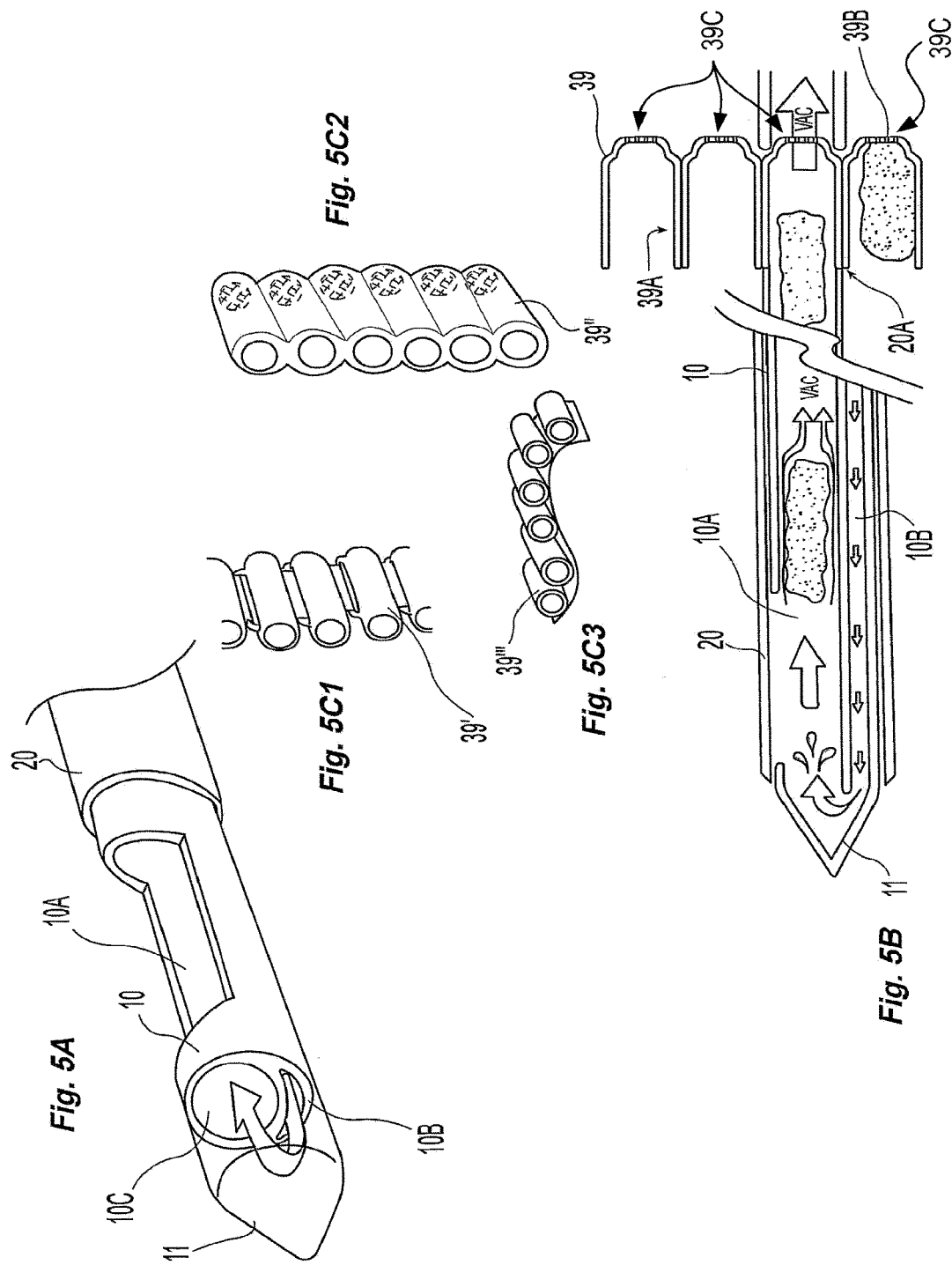

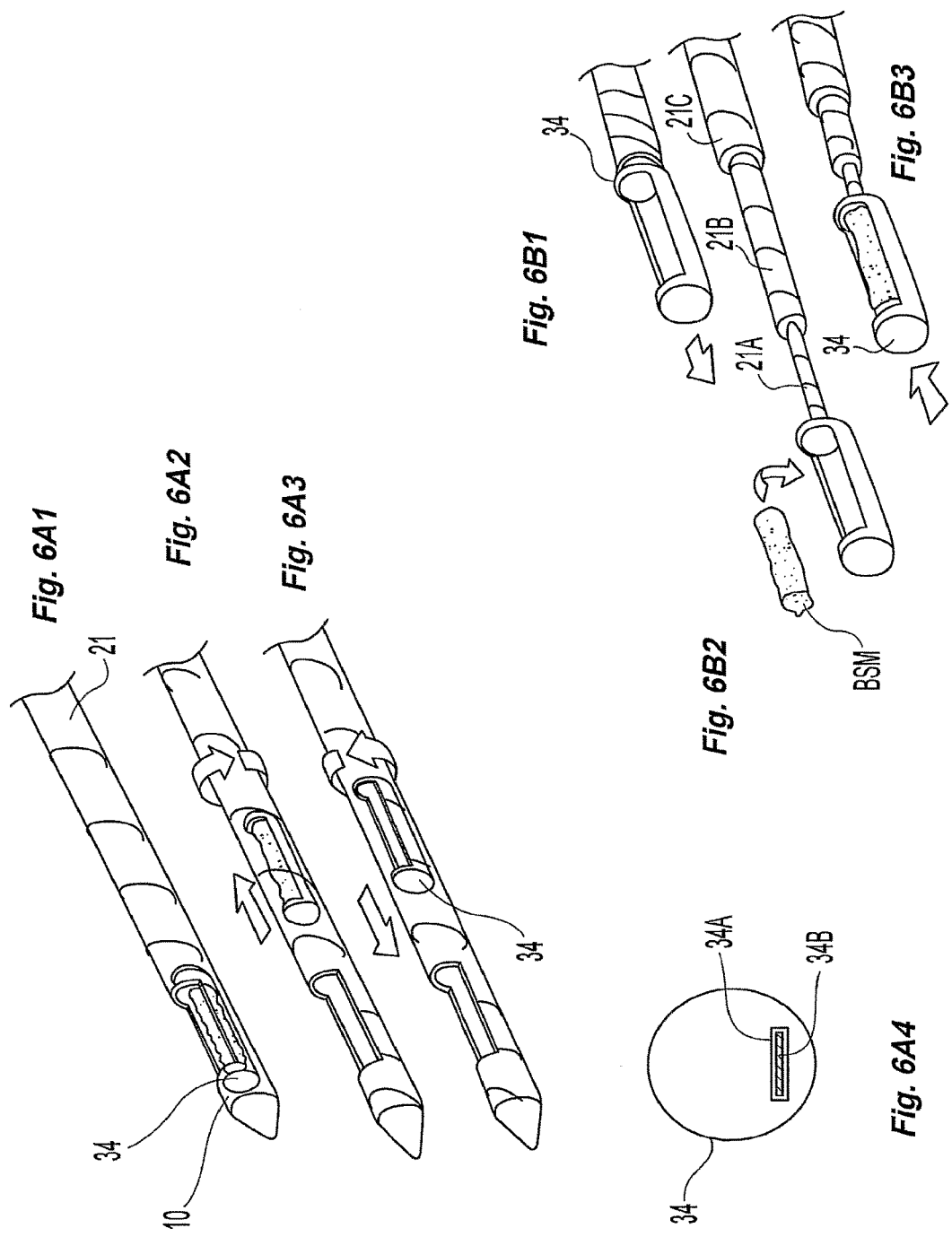

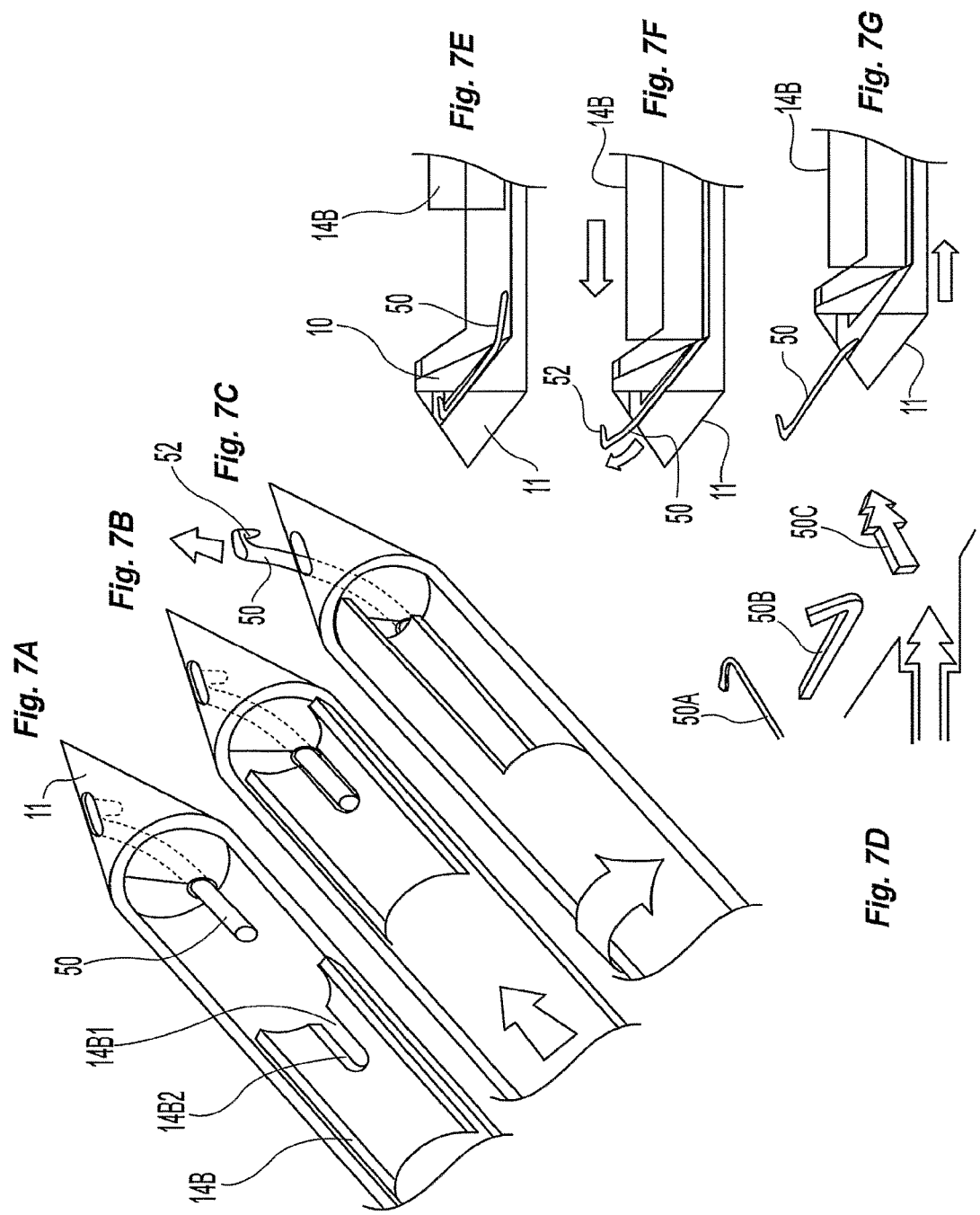

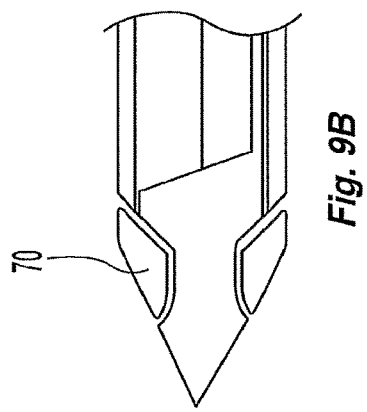
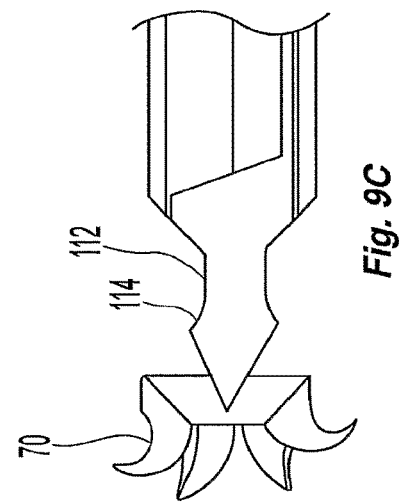
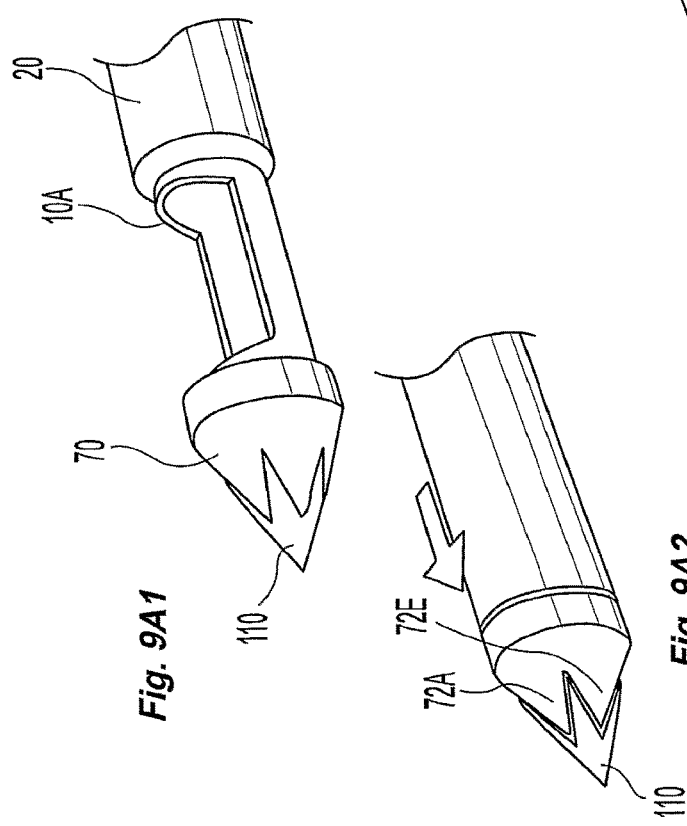

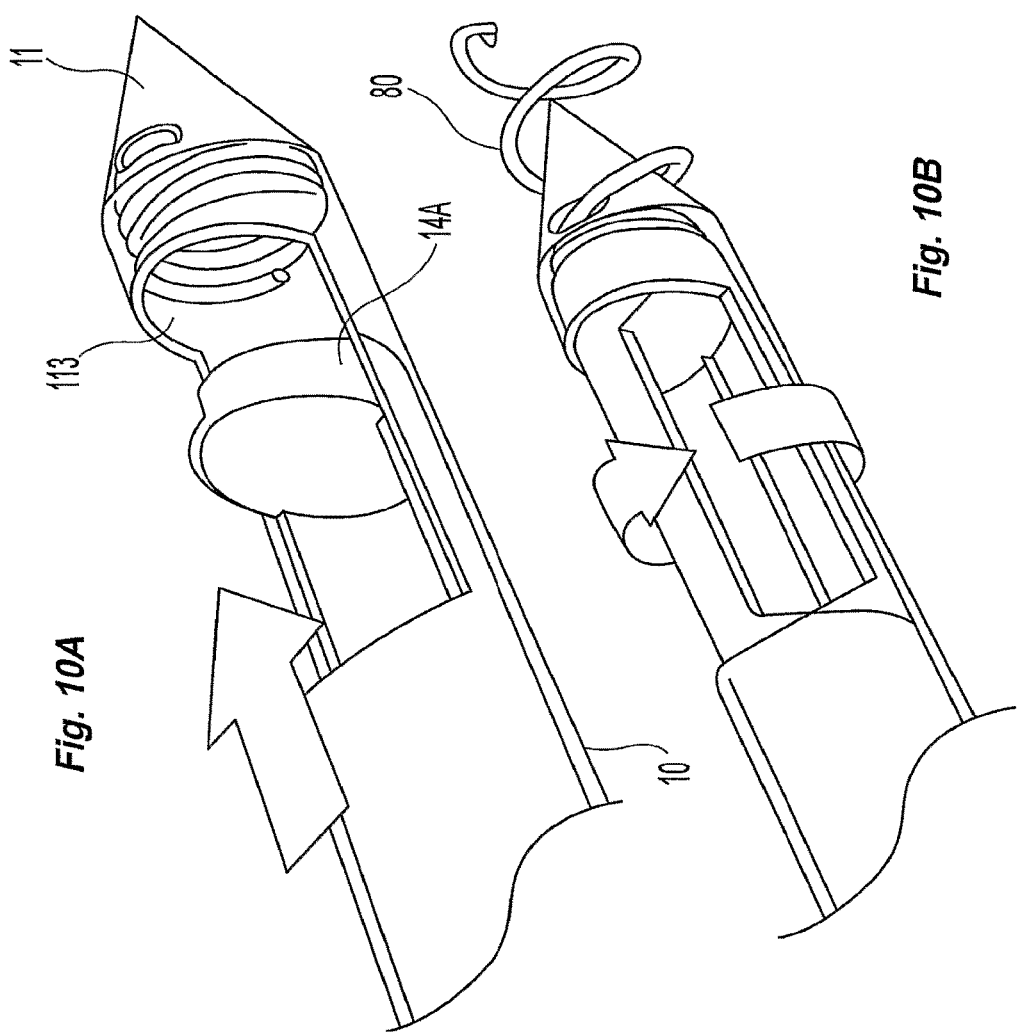

Fig. 11
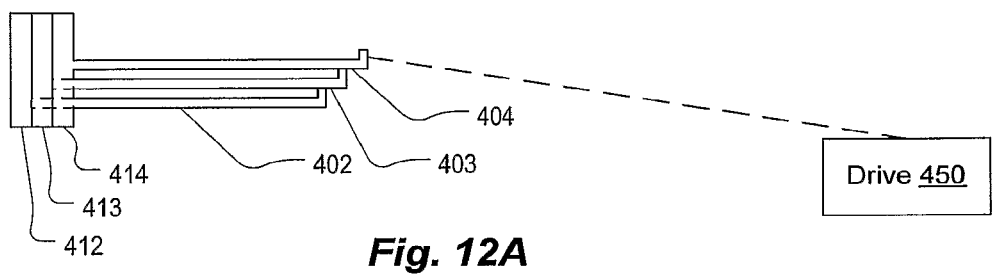
Fig. 12A
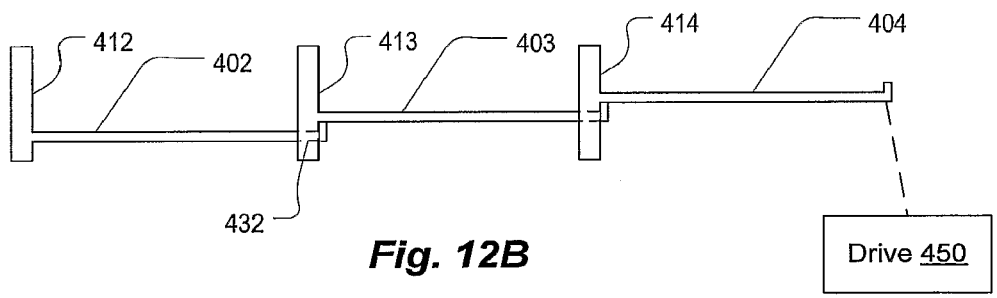
Fig. 12B

SINGLE-INSERTION, MULTIPLE SAMPLING BIOPSY DEVICE USABLE WITH VARIOUS TRANSPORT SYSTEMS AND INTEGRATED MARKERS

PRIORITY DATA AND INCORPORATION BY REFERENCE

This application is a continuation of U.S. patent application Ser. No. 13/608,609 filed Sep. 10, 2012, now U.S. Pat. No. 8,961,430, which is a divisional of U.S. patent application Ser. No. 11/997,404 filed Jul. 7, 2008, now U.S. Pat. No. 8,282,574, which is a U.S. national application under 35 U.S.C. 371 of International Application No. PCT/US2006/031326, filed Aug. 10, 2006, which claims benefit of priority to U.S. Provisional Patent Application Ser. No. 60/707,228 filed Aug. 10, 2005, each of which is incorporated by reference in its entirety.

FIELD OF THE INVENTION

This invention relates to a tissue biopsy sampling device.

BACKGROUND OF THE INVENTION

It is sometimes desirable or necessary to obtain specimens of tissue from humans and other animals, particularly in the diagnosis and treatment of patients with cancerous tumors, premalignant conditions, and other diseases or disorders. For example, when it is discovered that suspicious conditions exist, either by means of x-ray or ultrasound imaging in various tissues of the body, a physician usually performs a biopsy to determine if the cells at the suspected site are cancerous or benign.

A biopsy can be done either by an open or percutaneous technique. Open biopsy is an invasive procedure using a scalpel, by either a portion (incisional biopsy) being removed or the entire mass (excisional biopsy) is removed. Percutaneous biopsy is usually done with a needle-like instrument through a relatively small incision, and can be performed by fine needle aspiration (FNA) or through the taking of a core biopsy sample. In FNA biopsy, individual cells or clusters of cells are obtained for cytologic examination and can be prepared such as in a Papanicolaou smear. In a core biopsy, a core or fragment of the tissue is obtained for histological examination.

Uncontaminated and intact tissue from the organ, lesion, or tumor is preferred by medical personnel in order to arrive at a definitive diagnosis regarding the patient's condition. In most cases only part of the tissue in question needs to be sampled. The portions of tissue extracted must be indicative of the organ, lesion, or tumor as a whole. Often, multiple tissue samples from various locations of the mass being sampled may be taken.

The percutaneous biopsy procedure can be performed utilizing various techniques and devices. One such biopsy device can include an inner stylet positioned inside an outer cannula, where the stylet is able to slide into and out of the cannula. The stylet can be a solid, pointed needle having a tissue sampling recess, and the cannula can be a hollow, open-ended needle having a sharp tip. The stylet and cannula can be manipulated cooperatively to capture a tissue sample in the sample recess. Such existing devices can be manually operated, semi-automated, and automated.

U.S. Pat. No. 6,485,436 shows a multiple sample biopsy needle with a hydraulic mechanism that circulates fluid from the tip of the needle back to a receiving basket or baskets. A revolver-type array of receiving chambers is disclosed.

U.S. Pat. No. 5,827,305 shows a tissue sampling needle that pushes a sample proximally using a saline wash. Samples remain spaced apart within the needle such that the sequence of their collection is preserved. Samples can also be removed from a port while the needle remains in place. No mechanical transport mechanisms or drives are disclosed.

U.S. Pat. No. 5,526,822 shows a transport system that uses a cannula and knock-out pin combined with a vacuum source to shuttle a tissue sample to a multiple-chamber cassette where it is knocked out. The cannula is then repositioned for another sample. The vacuum source is external. A revolving sample cassette is also shown. A vent opening in each sample cylinder of the cassette is provided to eject the fluid used to transport the tissue sample. A removable disposable needle-bearing cassette interfaces with rotary and linear drives by means of long gears and shuttles that cradle the gears. Cutters operate in rotary and linear fashion (a counter-rotating cutters embodiment is included) and the cannula can be rotated to orient the sample opening.

U.S. Pat. No. 6,017,316 shows a transport system similar to U.S. Pat. No. 5,827,822 in which a cutter transports with vacuum assist. Multiple sampling with single insertion is described but not automated multiple sample-handling. The details of a drive system are not disclosed.

U.S. Pat. No. 6,193,673 shows a needle with a durable part and a disposable part. An external cutting cannula rotates and advances axially to cut a sample. The tissue cutter is driven axially by a rack and pinion drive which are part of a durable component. A cradle connects the rack to the cutting cannula.

U.S. Pat. No. 5,944,673 describes a tissue extractor that rotates within a piercing needle to align with any one of multiple receiving ports while obstructing the remaining ports. The tissue sample is cut by advancing the cutter and removing by withdrawing the extractor. A vacuum holds the tissue sample in place during the removal of the tissue extractor from the cutter. The cutter rotates as it advances.

It is known to obtain a single sample with a single insertion. However, there are circumstances where there may be a need to obtain more than one samples. While the known biopsy needle can be re-inserted multiple times, such technique can cause pain and scarring of the body site.

It is known to leave a marker at the biopsied site. To do so, however, a physician or healthcare provider would typically need to withdraw the biopsy needle and insert a different device to leave a marker at the biopsied site. The additional step with the marker device concurrent with the tissue sampling may not allow the marker to be deposited at the actual biopsied site, which can lead to inaccurate post-biopsy diagnosis.

SUMMARY OF THE INVENTION

The present invention provides for exemplary embodiments of a single-insertion, multiple sampling biopsy device. The present invention also provides for exemplary embodiments of a single-insertion, multiple sampling device with integrated marker release.

According to an embodiment, a biopsy device has a stylet with a distal end and a proximal end, a sample opening being provided at the distal end. An interior volume lies within the stylet and runs between the distal and proximal ends. The sample opening provides access to the interior volume. The stylet has a recovery position proximal of the distal end. A shuttle is mounted in the stylet and free to travel from the sample opening to the recovery position. The shuttle has at least one bulkhead shaped and positioned to push a sample in the shuttle toward the proximal end of the stylet. For example, the shuttle could be a trough-shaped car that is transported along the stylet. A transport subassembly may be provided which is coupled to the shuttle. The shuttle may have at least one bulkhead positioned such that is moves any tissue sample placed therein from the sample port to the proximal end of the stylet. In use, this embodiment allows a sample to be drawn into a sample opening and into the shuttle. Once separated, the sample is carried to the recovery position at the proximal end of the stylet by the shuttle.

In a refinement of the above embodiment, the transport subassembly has a second shuttle (or more shuttles) may be provided which nests at least partly within the first (and others). In this case, multiple samples may be carried by a train of shuttles with the most deeply nested shuttle carrying a first sample and the non-nested one carrying the last. In this way, the transport subassembly moves the first shuttle and the second shuttle consecutively (and potentially further shuttles) to transport respective samples. In the above variations, within each shuttle or adjacent thereto, a bulkhead with a surface at least partly normal to a direction of travel thereof, may be provided to help push the samples in the proximal direction. For example, the bulkhead may be a wall of a trough-shaped cart. If provided, the second shuttle nested at least partly within the first, each shuttle may have a distal bulkhead that has a surface at least partly normal to a direction of travel thereof.

The transport subassembly may have a spooling tape that winds and unwinds to transport the shuttle in the proximal and distal directions. The spooling tape may wind and unwind to transport the shuttle in proximal and distal directions with the shuttle being defined by a distal portion of the tape.

The transport subassembly can have a loop that runs between the opening and the recovery position with the shuttle connected to the loop and the loop winding (and/or potentially unwinding) to transport the shuttle through the stylet. The stylet may have a recovery port at the recovery position and may include a recovery member with an engaging surface that engages the sample in the shuttle to move it out of the shuttle. The recovery member may be movable within the shuttle and may cause the engaging surface to move from a position in the shuttle toward the recovery port, whereby a sample in the shuttle may be removed from the shuttle through the recovery port.

In some embodiments, the transport subassembly may include a linear actuator. The stylet may have an internal surface with internal threads, with the linear actuator including a threaded cylindrical member having external threads that mesh with the stylet internal threads. The threaded cylindrical member may be rotatable within the stylet and rotatably coupled to the first shuttle. The stylet may have an internal surface with internal threads, the linear actuator may include a threaded cylindrical member having external threads that mesh with the stylet internal threads, the threaded cylindrical member may be rotatable within the stylet and rotatably coupled to the first shuttle and the first shuttle may have a member in engagement with the stylet that prevents the rotation of the first shuttle within the stylet. The linear actuator may include threaded cylindrical members having external and internal threads distributed among them such that when the cylindrical members are nested, one within another, mating pairs of the external and internal threads are in mesh, one of the cylindrical members may be rotatably coupled to the first shuttle.

The linear actuator may include threaded cylindrical members having external and internal threads distributed among them such that when the cylindrical members are nested, one within another, mating pairs of the external and internal threads are in mesh. Then, one of the cylindrical members may be rotatably coupled to the first shuttle. The first shuttle may have a member in engagement with the stylet that prevents the rotation of the first shuttle within the stylet.

According to another embodiment, a biopsy device has a stylet with a distal end and a proximal end. The stylet has a sample opening and an interior volume adjacent its distal end. The opening provides access to the interior volume and the stylet has a recovery position proximal of the distal end. A resilient tape, with a distal end that is guided by the stylet is movable along the stylet in proximal and distal directions. The stylet may have an edge guide that receives the tape distal end and which, when the tape distal is moved in the distal direction, shapes the tape distal end into an open shape that defines a recess to allow a sample to be received in the recess. The tape distal end may return to a closed shape when moved proximal of the edge guide thereby securing the sample for transport.

According to another embodiment, a biopsy device has a stylet with a distal end and a proximal end. The stylet has a sample opening near the distal end and a recovery position near the proximal end. The stylet has an interior volume adjacent the stylet distal end, the opening providing access to the interior volume. Also provided is a cassette with multiple recesses, each having an access and a fluid-permeable blind end. The cassette is positioned at the recovery position to align a selected one of the cassette recesses with the recovery position such that the selected cassette recess is in fluid communication with the interior volume of the stylet. A transport mechanism forces a fluid from the stylet distal end toward the stylet proximal end such that fluid exits the blind end of the selected cassette recess, whereby a specimen is flushed into the selected cassette recess and is caught by it. The transport mechanism may include a storage container and transports fluid from the storage container to the stylet distal end.

The transport mechanism may include a reservoir, a pump, and a three way valve. The stylet may include a fluid lumen adjacent the interior volume. The three way valve may connect the fluid lumen, the reservoir, and the pump. The transport mechanism may operate the pump and the three way valve to transport fluid from the reservoir to the stylet distal end during a transport cycle and to recover fluid remaining in the fluid lumen by returning the fluid to the reservoir, during a reset cycle.

According to another embodiment, a biopsy device has a stylet having distal and proximal ends, a harvest position, at the distal end, where tissue samples are received, and a delivery position proximal of the harvest position. The stylet may have a marker held at the stylet distal end with a transport member within the stylet. The transport member may be movable in an axial direction between the harvest and delivery positions to receive samples at the harvest end and deliver samples at the delivery end. The transport member may be further movable beyond the harvest position, or further movable in a direction other than the axial direction, to push at least a portion of the marker to a position that causes the marker to be deployed. The transport member may be further movable beyond the harvest position to push at least a portion of the marker to a position that causes the marker to be deployed. The transport member may be further movable in a direction other than the axial direction to push at least a portion of the marker to a position that causes the marker to be deployed. The marker may include a wire coil which may be housed by the stylet prior to deployment and which may be deployed by rotating the transport member around the axial direction. The transport member may have a distal edge having a recess, the marker may include a hook which may be housed by the stylet prior to deployment and which may be deployed by rotating the transport member around the axial direction to move the recess away from the marker such that when the transport member may be advanced distally, the marker may be pushed by the distal edge.

The stylet may have a tip and the marker may include a deformable member that may be elastically secured to the tip, the marker may be deployable by moving the transport member beyond the harvest position to push the marker from the tip. The marker may include a split ring that may be elastically secured to the tip. The marker may be deployable by moving the transport member beyond the harvest position to push the marker from the tip. The marker may include a flexible member that may be elastically secured to the tip.

The transport member may have a distal tip with a ramp and the marker may have a deformable part that may be proximal of the ramp. In this case, the transport member may cause the deformable part to deform when the transport member may be moved proximally of the harvest position. The marker may have a blooming part that may be proximal of the ramp so that the transport member causes the deformable part to bloom when the transport member is moved proximally of the harvest position.

According to an embodiment, a biopsy device has a stylet with distal and proximal ends and a sample opening within an interior volume adjacent its distal end. The opening provides access to the interior volume. The stylet has a recovery position proximal of the distal end where samples are removed from the stylet. A shuttle mounted in the stylet is free to travel from the sample opening to the recovery position. The shuttle has at least one bulkhead shaped and positioned to push a sample in the shuttle toward the proximal end of the stylet. A transport subassembly coupled to the shuttle bulkhead moves a tissue sample from the sample port to the proximal end of the stylet. A second shuttle can be nested at least partly within the first to allow additional samples to be recovered without removing the needle.

The nested shuttles are preferably located at the sample opening. In this case, the transport subassembly moves the shuttles consecutively to transport respective samples to the recovery position. Preferably the shuttles are used once in a disposable needle portion so there is no need to place the shuttles back to the opening after transporting them to the recovery position.

Preferably, the shuttle has a distal bulkhead with a surface at least partly normal to a direction of travel so that that the distal bulkhead can push the sample in the proximal direction. The shuttles can be open at the bottom or closed.

In an alternative embodiment, the transport subassembly includes a spooling tape that winds and unwinds to transport the shuttle in a proximal direction. To harvest multiple samples, the tape can be extended and rewound repeatedly. The shuttle can be defined by the shape of a distal part of the tape in this case. The distal end of the tape preferably wraps naturally into a closed shape which is opened by engaging edges of the tape in slots at the distal end of the stylet. When the tape is pulled proximally, the edges disengage from the slots and the sample is held by the closed shape and protected from rubbing against the stylet as it is transported.

In another embodiment, the transport subassembly has a loop that runs between the opening and the recovery position, the shuttle being connected to the loop and the transport subassembly winding the loop to transport the shuttle through the stylet. Preferably, the stylet has a recovery port at the recovery position. A recovery member with an engaging surface is movable within the shuttle while at the recovery position so as to cause the engaging surface to move from a position in the shuttle toward the recovery port. In this way a sample in the shuttle is removed from the shuttle through the recovery port.

In another embodiment, the transport subassembly includes a linear actuator. One type of linear actuator employs threads on the internal surface of the stylet and a threaded cylindrical member with external threads that mesh with the stylet internal threads. The threaded cylindrical member is rotatable within the stylet and rotatably coupled to the first shuttle. Preferably, a longitudinal member in engagement with the stylet and the shuttle prevents the rotation of the shuttle within the stylet. In a variation of this, the linear actuator includes multiple threaded cylindrical members having external and internal threads distributed among them such that when the cylindrical members are nested, one within another, mating pairs of the external and internal threads are in mesh, one of the cylindrical members being rotatably coupled to the first shuttle. In this case, also, preferably, a longitudinal member in engagement with the stylet and the shuttle prevents the rotation of the shuttle within the stylet.

According to yet another embodiment, the biopsy device has a stylet having a distal end and a proximal end, the stylet having a sample opening near the distal end and a recovery position near the proximal end. The stylet has an interior volume adjacent the stylet distal end, the opening providing access to the interior volume. There is a cassette with multiple recesses, each having an access and a fluid-permeable blind end, positioned at the recovery position to align a selected one of the cassette recesses with the recovery position. The alignment is such that the selected cassette recess is in fluid communication with the interior volume of the stylet. A transport mechanism forces a fluid from the stylet distal end toward the stylet proximal end such that fluid exits the blind end of the selected cassette recess, whereby a specimen is flushed into the selected cassette recess and is caught by it.

Preferably, the transport mechanism includes a storage container and transports fluid from the storage container to the stylet distal end. More preferably, the transport mechanism includes: a reservoir, a pump, and a multi-way valve and the stylet includes a fluid lumen adjacent the interior volume. Preferably, the three way valve connects the fluid lumen, the reservoir, and the pump and the transport mechanism operates the pump and the multi-way valve to transport fluid from the reservoir to the stylet distal end during a transport cycle and to recover fluid remaining in the fluid lumen by returning the fluid to the reservoir, during a reset cycle. Preferably, the cassette recesses are linked together by flexible connections to form a bandolier.

Also, preferably, a vacuum source of the transport mechanism includes a vacuum connection from the vacuum source to the selected recess blind end to aid in drawing a specimen into the selected recess. In this case, preferably, the stylet has two parallel lumens, a primary lumen for transporting specimens and a secondary lumen for conveying fluid a proximal end of the stylet to the distal end of the stylet where the fluid returns through the primary lumen. The stylet has a sample opening for receiving specimens from a host at its distal end and the stylet carries a cutting cannula that surrounds the stylet and selectively covers the sample opening, the drive mechanism conveying fluid to transport specimens only when the cutting cannula covers the sample opening.

In another embodiment, a biopsy sample extraction needle has a sample extraction end, recovery end, and a transport channel linking the extraction and recovery ends. A pump with a multi-way valve is connected to a fluid reservoir linked to the transport channel such that the pump can: draw a vacuum at at least the transport end with the multi-way valve in a first setting, draw fluid from the reservoir with the multi-way valve in a second setting, and flush the transport channel from the extraction end to the recovery end to transport a sample through the transport channel with the multi-way valve in a third setting.

Preferably, the first and third multi-way valve settings are identical. The pump is preferably a syringe which forms a part of disposable, single-use sterile set. The pump can recover residual saline from the transport channel and deliver it to the reservoir. A volume-reducing valve is preferably provided to reduce a total sealed volume in fluid with the recovery end when the vacuum is drawn by the pump. As a result of this, the vacuum can be stronger when the sample is harvested. The valve can be released after the sample is obtained. The valve can be a tube pinch valve that is part of the lumen through which samples are transported.

In another embodiment, a biopsy device has a tissue extraction portion and a recovery portion, remote from the tissue extraction portion. A channel connects the tissue extraction portion and the recovery portion. Preferably, the biopsy device includes a biopsy needle. The tissue extraction portion has a receiving lumen and a cutting blade. A syringe and a flow controller have a first configuration in which the syringe draws a vacuum at the tissue extraction portion, which in turn draws tissue from a host into the receiving portion. The syringe and flow controller have a second configuration in which the syringe flushes fluid from the tissue extraction portion to the recovery portion to transport tissue samples thereto.

Preferably a disposable component is provided as a sterilized single-use component which includes the syringe and a durable component that houses a motor to drive the syringe. Preferably, the syringe and flow controller have a third configuration in which the syringe draws fluid from a reservoir before flushing the fluid from the tissue extraction portion to the recovery portion.

In another embodiment, a biopsy device has a stylet with distal and proximal ends, a harvest position, at the distal end, where tissue samples are received, and a delivery position proximal of the harvest position. The stylet has a marker held at the stylet distal end. A transport member within the stylet is movable in an axial direction between the harvest and delivery positions to receive samples at the harvest end and deliver samples at the delivery end. The transport member is further movable beyond the harvest position, or further movable in a direction other than the axial direction, to push at least a portion of the marker to a position that causes the marker to be deployed.

Preferably, the transport member is further movable beyond the harvest position to push at least a portion of the marker to a position that causes the marker to be deployed. Alternatively, the transport member is further movable in a direction other than the axial direction to push at least a portion of the marker to a position that causes the marker to be deployed. In an embodiment, the marker includes a wire coil which is housed by the stylet prior to deployment and which is deployed by rotating the transport member around the axial direction.

In another embodiment of the marker device, the transport member has a distal edge having a recess, the marker includes a hook which is housed by the stylet prior to deployment and which is deployed by rotating the transport member around the axial direction to move the recess away from the marker such that when the transport member is advanced distally, the marker is pushed by the distal edge.

In yet another embodiment of the marker device, the stylet has a tip and the marker includes a deformable member that is elastically secured to the tip, the marker being deployable by moving the transport member beyond the harvest position to push the marker from the tip. In still another embodiment, the stylet has a tip and the marker includes a split ring that is elastically secured to the tip, the marker being deployable by moving the transport member beyond the harvest position to push the marker from the tip.

In another embodiment, the stylet has a tip and the marker includes a flexible member that is elastically secured to the tip. The marker is deployable by moving the transport member beyond the harvest position to push the marker from the tip. In this case, the transport member preferably has a distal tip with a ramp and the marker has a deformable part that is proximal of the ramp, the transport member causing the deformable part to deform when the transport member is moved proximally of the harvest position. Preferably, the transport member has a distal tip with a ramp and the marker has a blooming part that is proximal of the ramp. The transport member causes the deformable part to bloom when the transport member is moved proximally of the harvest position.

In an embodiment, a method of performing a tissue biopsy includes severing a tissue sample from a host within a shuttle located inside a biopsy needle, the shuttle being movable within the biopsy needle, holding the tissue sample in the shuttle while moving the shuttle from a distal end of the biopsy needle to a proximal end to transport the tissue sample, and repeating the severing and holding steps without removing the biopsy needle from the host. In a preferred embodiment, the shuttle is connected to a loop and the moving includes revolving the loop around endpoints located at the distal and proximal ends. In another preferred embodiment, a removal member is extended into the shuttle at the proximal end and removing it from the shuttle.

Preferably, the method includes applying a vacuum to the biopsy needle prior to severing the tissue sample. In an embodiment, moving of the shuttle includes retracting a linear actuator or, in yet another embodiment, it includes rotating a threaded lumen to which the shuttle is threaded. A first instance of the severing and holding steps to transport a first sample is preferably done with a different shuttle from a second instance. More preferably, moving the shuttle includes separating it from a nested set of shuttles.

In another embodiment, a method of performing a tissue biopsy includes transporting an excised tissue sample to the end of a flat elongate member held within a biopsy needle. The transporting includes wrapping the end of the elongate member over the sample to prevent it from rubbing against the biopsy needle. Preferably, the elongate member is elastic at its end and the wrapping is a result of the release of a deformation of the elongate member end. Also, preferably, the transporting includes wrapping the elongate member about a spool.

In another embodiment, a tissue biopsy includes drawing a vacuum in a biopsy needle with a pump to move a portion of a host to be sampled into the biopsy needle for excision and transporting an excised sample of the host through the needle by flushing fluid from the pump. Preferably, the pump is a syringe. Preferably, the pump has a chamber and the vacuum is drawn by expanding the chamber and the fluid is flushed by compressing the chamber. Also, preferably, the vacuum is drawn by expanding the chamber and the flushing includes filling the chamber by expanding it while in fluid communication with a fluid reservoir and subsequently compressing the chamber to expel the fluid.

In another embodiment, a method of performing a tissue biopsy includes cutting a tissue sample by axially moving a cutting cannula of a biopsy needle relative a stylet that holds a sample within the cutting cannula in a first direction and deploying a marker by moving the at least a portion of the stylet in a second direction relative to the cutting cannula. Preferably, the marker is a split ring held on the stylet until pushed off by the cutting cannula. Alternatively the marker is a hook and the deploying is performed by rotating a shuttle held by the stylet.

According to another embodiment, a multiple sample biopsy device has a sampling mechanism that cuts tissue samples and a flexible sock wrapped over a support so as to define a recess holding open an access to the sock. A transport mechanism conveys a first tissue sample into the recess of the sock and partially everts by pulling a blind end thereof thereby extending a length of the recess to provide room for another sample and simultaneously transporting the first tissue sample along a direction of the pulling. Preferably, the sampling mechanism includes a hollow cannula having an interior, the sock being located in the interior. Preferably, the sock is of a mesh. The sample can be moved into the sock using suction or by pushing it with fluid. The sample can be drawn into the sock just by moving the sock like a 360 degree conveyor belt. In that case fluid could be provided to just lubricate the sample. Also, the sock is preferably porous and the transport mechanism conveys tissue samples into the recess by flushing against the sample pushing it into the recess and wherein the fluid flows out of the sock. Alternatively a vacuum can be used to pull the sample into the sock. The vacuum can be the same vacuum provided for drawing the sample into the sample recess before cutting the sample.

According to another embodiment, a multiple sample biopsy device has a sampling mechanism that cuts tissue samples. The device has a flexible sock with an access to the sock interior, the sock being an elongate member having a longitudinal axis. A transport mechanism conveys a first tissue sample into the recess of the sock after a first tissue sample is cut and conveys a second tissue sample into the recess of the sock after the second tissue sample is cut such that the tissue samples are arranged in a row along the longitudinal axis. Preferably, the sampling mechanism includes a hollow cannula having an interior, the sock being located in the interior. Preferably, the sock is of a mesh. Preferably, the sock is porous and the transport mechanism conveys tissue samples into the recess by flushing against the sample pushing it into the recess and wherein the fluid flows out of the sock. Preferably, when the transport mechanism conveys a first tissue sample into the recess of the sock, it partially everts the sock by pulling a blind end thereof thereby extending a length of the recess to provide room for the second sample and simultaneously transports the first tissue sample along a direction of the pulling. Alternatively, when the transport mechanism conveys a first tissue sample into the recess of the sock, it partially everts the sock by pulling a blind end of the sock along the longitudinal axis thereof, thereby extending a length of the recess to provide room for the second sample and simultaneously transports the first tissue sample along the longitudinal axis.

According to another embodiment, a method of performing a tissue biopsy includes, in a biopsy needle, cutting a succession of tissue samples and forcing each in turn into a sock, aligning them along the length of the sock and removing the biopsy needle and recovering the tissue samples by removing the sock. Preferably, the order of the samples in the sock at the end of the method corresponds to the order in which the samples were cut.

According to another embodiment of a multiple sample biopsy device a sampling mechanism cuts tissue samples and a chain of paddles connected together such that they can be nested together and pulled as a chain by expanding the chain by pulling only one of the paddles. The sampling mechanism conveys a first tissue sample adjacent a first one of the paddles on a proximal side thereof. A drive moves the first one in the proximal direction less than a distance required for the first one to engage a second adjacent one of the paddles such that the first paddle moves the first tissue sample proximally without causing the second paddle to move. The sampling mechanism conveys a second tissue sample adjacent a second one of the paddles on a proximal side thereof. The drive moves the second one in the proximal direction less than a distance required for the second one to engage a third adjacent one of the paddles such that the first and second paddles move the first and second tissue samples, respectively, without causing a third of the paddles to move. Preferably, the sampling mechanism includes a hollow cannula having an interior, the chain of paddles being arranged in a series within and along the interior.

In all of the above devices, a vacuum source and a power source may be provided in a self-contained hand-held biopsy device. In all of the methods, a biopsy unit may contain a controller programmed to execute the methods automatically or contingent on consecutive command being entered through the biopsy device.

BRIEF DESCRIPTION OF THE DRAWINGS

The accompanying drawings, which are incorporated herein and constitute part of this specification, illustrate presently preferred exemplary embodiments of the invention, and, together with the general description given above and the detailed description given below, serve to explain features of the invention.

FIGS. 1A-1D illustrate a transport subassembly for a biopsy device according to one exemplary embodiment of the present invention.

FIGS. 2A-2E illustrate another transport assembly.

FIGS. 3A and 3B illustrate yet another biopsy transport system.

FIGS. 4A-4C illustrate yet another tissue transport system for a biopsy device.

FIGS. 5A-5H and 5J illustrate a tissue transport system utilizing saline for deposit into a bandolier type collection chamber.

FIGS. 6A1-6A4 illustrate a tissue transport using a threaded type inner cannula.

FIGS. 6B1-6B3 illustrate a tissue transport using a telescoping drive.

FIGS. 7A-7G illustrate an integrated biopsy marker system for each of the transport assembly of FIGS. 1-6.

FIGS. 9A1, 9A2, 9A3, 9B and 9C illustrate a further integrated biopsy marker system for each of the transport assembly of FIGS. 1-6.

FIGS. 10A and 10B illustrate yet another integrated biopsy marker system for each of the transport assembly of FIGS. 1-6.

FIG. 11 shows a controller.

FIGS. 12A and 12B show an embodiment of a paddle transport mechanism.

DETAILED DESCRIPTION OF THE PREFERRED EXEMPLARY EMBODIMENTS

Figure 5D:
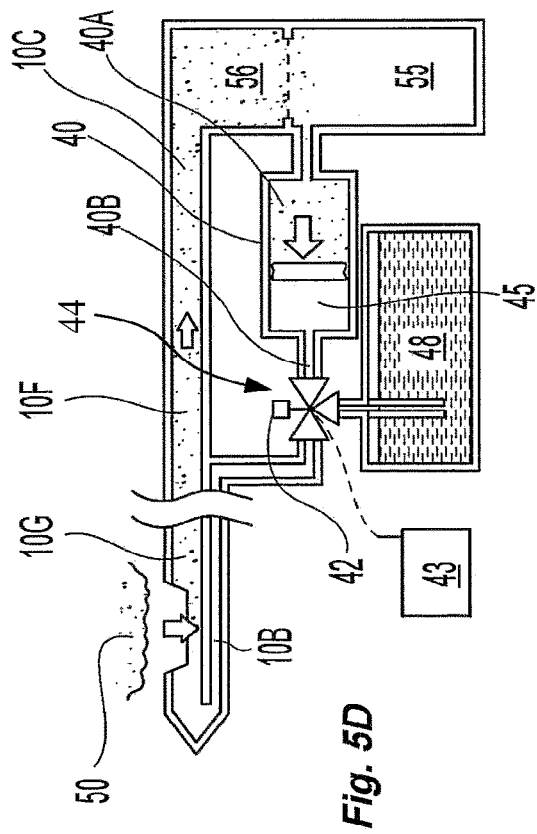

FIGS. 1-10 illustrate the preferred exemplary embodiments which utilize the same reference numeral to indicate generally similar components. In particular, FIG. 1A shows a perspective view of a stylet 10 coupled to the single-insertion, multiple samples biopsy transport subassembly 100 having distal end 100A and proximal end 100B that can be implemented in a multiple sampling biopsy device (not shown). The transport subassembly 100 includes the stylet 10, which has a tip 11 at the distal end 100A and an outer cutting cannula 20 covering a substantial portion of the stylet 10 and a first port 10A. Extending through a hollow portion of the stylet 10 are a plurality of nested paddles 12, 14, 16, and 18 coupled to a drive unit at the proximal end 100B, and other ancillary components of the device 100 such as respective saline or vacuum reservoirs, motor drive, reduction gears, switches and sensors (not shown).

The transport subassembly 100 operates by retracting the outer cannula 20 proximally to expose the first port 10A. Vacuum can be provided to the lumen 10B with orifices 10C to allow the lumen 10B to siphon biological tissue into the port 10A (FIG. 1A). The outer cannula 20 is extended distally to sever the tissue BSM from its main mass. Alternatively, a cannula disposed internally of the stylet 10 can also be used. Once the tissue BSM has separated from the main mass, two of the paddles 12 and 14 are retracted proximally. The longitudinal distance between the two paddles and the port 10A partly define the size of tissue sample per retraction of the two paddles. As shown in FIG. 1B, the device is now ready for a subsequent sample with paddles 14 and 16. As shown in FIG. 1C, to ensure that the plurality of paddles can be retained in the stylet 10 without reducing the internal volume that would be needed to transport the tissue BSM through the internal passage of stylet 10, each paddle and its corresponding connector can be mounted in an arcuate offset configuration.

Referring to FIGS. 12A and 12B, in an embodiment, the paddles 412, 413, 414 are linked together as a chain so that only the most proximal one 414 of the paddle elements needs to be moved by a drive 450. Thus, moving the most proximal paddle 414 first a particular distance in a proximal direction, which distance is less than or equal to a link 404 length, will not cause the next paddle 413 to move. But a further movement will cause the most proximal paddle 414 to engage the next paddle 413 causing it to move. Paddle 413 would then engage the next paddle 412 after it is moved beyond the length of its link 403. If a sample is received and moved by the paddle 414 while leaving the other paddles in place, then the drive 450 only needs to move the paddles 412, 413, and 414 in a single direction for multiple samples. The final result after multiple samples is shown in FIG. 12B. The links 402, 403 may be guided by openings or slots in the proximal adjacent paddle, for example as indicated at 432.

In addition, to ensure the paddles don't move until positively engaged by the proximally adjacent paddle, the paddles themselves may be frictionally engaged within a surrounding cannula. This friction would be overcome by the drive 450.

Referring to FIG. 2A, a flexible transport mechanism is shown and described. In this embodiment, the transport trough 22A can be a similar material as extension 22B. Alternatively, the trough 22A can be an arcuate sectioned polymer tube 22A coupled to a flexible extender 22B, which is winds onto a roller 24. As is the case above, an outer cannula 20 (not shown for clarity) is used to sever the tissue from its main mass. Alternatively, a cannula disposed internally of the stylet 10 can also be used. Thereafter, the extender 22B is rolled counterclockwise to move the section 22A proximally. To ensure that the arcuate section 22A can retain the tissue sample on the surface 22C, the stylet 10 can be provided with tracks 23A and 23B to allow the section 22A to be flattened due to the plastic material of the section 22A as the extender 22B is moved distally. When the extender 22B is moved proximally, the edges of the section 22A can disengage from the rails 23A and 23B, thereby allowing the flexible arcuate section 22A to fold inward forming a folded-in configuration 22D. This folding in of the polymer section 22A allows the section 22A to clamp over the biopsy sample (FIG. 2C) for transport proximally. As the sample is transported proximally, the sample enters an area of stylet 10 proximate port 20A. A keyed boss portion 26 can be provided inside the stylet 10 so that as the section 22A reaches the port the boss 26 spreads the polymer section 22A apart, from the closed configuration 22D, back to the open configuration of 22A, thereby releasing the grip on the tissue sample. At the same time, the boss 26 forces the tissue into a collection chamber (FIG. 2D). The extender 22B can be unrolled to move the polymer section 22A for engagement against tracks 23A and 23B for a subsequent tissue sampling. The extender 22B can be any suitable materials that allow for application of axial force distally to move the section 22A while permitting the extender 22B to be rolled in a circular configuration.

While in the foregoing embodiment, a boss 26 is illustrated as a means for spreading the closed section 22D to open it into the open configuration 22A to release the sample, other means for opening the section 22D are possible. For example, guides similar to rails 23A can be provided at the proximal end which catch the edges of the rolled section 22D and gradually unwrap it. Such guides could be provided in the form of an insert in the stylet 10.

Referring to FIG. 3A, another transport subassembly is provided. In this embodiment, the transport includes an inner cannula 28 surrounded by a nylon mesh tube (or "sock") 30. Nylon braid or weave having similar weight and elasticity similar to a woman's hose is suitable. This would allow the tube 30 to be stretched over the inner cannula 28 and to evert easily. Also, preferably, the tube 30 can be of hydrophobic material or have a hydrophobic surface to help prevent tissue samples adhering to it. For example a mesh coated with PolyTetraFluoroEthylene (PTFE) may be used.

A passageway 10B is provided to permit fluid communication between the mesh tube 30 and the passage 10B. In one embodiment, saline is provided via passage 10B while vacuum is provided in the mesh tube 30, which causes tissue BSM to be moved into the tube 30. A support tube 49 allows the mesh tube 30 to be everted over the inner cannula 28 as samples BSM are forced into it. Preferably the mesh tube 30 has a surface that helps to ensure positive engagement with samples, such as a surface covered with spines or hooks as illustrated. As each sample is drawn into the mesh tube 30, the mesh tube becomes ready to accept another sample. The mesh tube 30 itself may serve as a removable carrier that holds the samples BSM and separates them for delivery to a biopsy laboratory.

A saline flush may be provided to help ensure samples are moved into the mesh tube 30. This may provide lubrication as well as positive transfer into the mesh tube 30. The proximal end 32 of the mesh tube 30 may be pulled by a line 47. The drive mechanism for pulling the line 47 may include a pulley, for example. Extraction of the tissue BSM can be achieved by back flushing the tube 30 with saline, causing the sample to be ejected from the tube 30 as the tube 30 is counter-everted at a recovery position. In this case, the support tube 49 and the mesh tube 30 may be transported through the stylet 10 to recover position and the mesh tube 30 counter-everted by pulling at the leading edge 51 by a tow line (not shown).

After the samples are harvested, the mesh tube 30 can be removed from the biopsy device. The samples can remain in a row in the tube thereby keeping the samples organized according to the order in which they were taken.

As is the case above, an outer cannula 20 (not shown for clarity) is used to sever the tissue from its main mass. Alternatively, a cannula disposed internally of the stylet 10 can also be used, positioned in second port 20A.

Referring to FIG. 4A, a shuttle transport system utilizing pulleys is provided. In this system, a shuttle 34 (which defines a trough to receive tissue samples) is connected by a system of pulleys 36A, 36B, and belt or endless connector 36C. Orifices 34A can be formed on the underside of the shuttle 34 so that vacuum provided from a passage 10B can be used to siphon a tissue sample BSM from a main tissue mass. As is the case above, an outer cannula 20 (not shown for clarity) can be used to sever the sample from its main mass (FIG. 4B). Thereafter, the shuttle 34 is moved proximally towards port 20A via the system of pulleys and belt. Ejection of the sample BSM out of the port 20A can be accomplished by a series of plungers 34B that are sized for insertion through orifices 34A. Once the tissue BSM has been ejected into a collection vial or chamber (not shown), the shuttle 34 is translated towards port 10A for another collection of tissue (FIG. 4A).

Referring to FIG. 5A, a saline transport with a bandolier type collection cartridge is provided. In this embodiment, the stylet 10 is provided with a fluid passage 10B and main passage 10F. Fluid passage 10B can be connected via a suitable switching valve to allow saline to be pumped through the passage 10B in a distal direction while main passage 10F can be connected to a vacuum source to allow for saline and any other object entrained by the saline flow from passage 10B to flow through main passage 10F (FIG. 5B) and delivering the object (e.g.; tissue sample BSM) into a bandolier type collection cartridge 39. The bandolier cartridge 39 has design details that are believed to be advantageous. First, the bandolier cartridges 39 are designed to be indexed through a double sided port 20A so that each cartridge is indexed once through the stylet 10. Second, the cartridge has an open distal end 39A and a mesh material 39B formed over a proximal end to form a fluid permeable blind end 39C. This allows the tissue to be pushed through the open end 39A but to be retained by the mesh 39B at the fluid permeable blind end 39C with fluid maintaining its flow through the stylet 10. Third, the cartridges can be linked to each other via a flexible connector; chain link connection; or via a rigid connection.

FIGS. 5D-5H and 5J describe a saline pumping mechanism that may be used with the above and other embodiments. In FIG. 5D, a dual-action pump 40 (e.g., a syringe actuatable by a drive motor) can be used to generate negative pressure by forcing a piston 46 to expand the volume of a chamber 40A, which is in communication with the main passage 10F of the stylet 10. A four-way valve 44, with a vent 42 at one branch, is configured to empty the chamber 45 to the ambient through the four-way valve and out the air vent 42 as air is sucked into the chamber 40A. Note that the vent 42 may be fitted with a filter to prevent contamination leaking into the biopsy device.

The vacuuming action draws in a tissue sample 53. To trigger the cutting of the sample, sensors (not shown) may be used to detect the movement of the tissue sample 53 into the lumen 10B, or the passage of an elapsed time interval or user action may be used to determine that a sample 53 has been drawn into the passage 10B. The outer cannula 20 can be used to sever the tissue sample from the host. Alternatively, a cannula disposed internally of the stylet 10 can also be used.

Figure 5E:
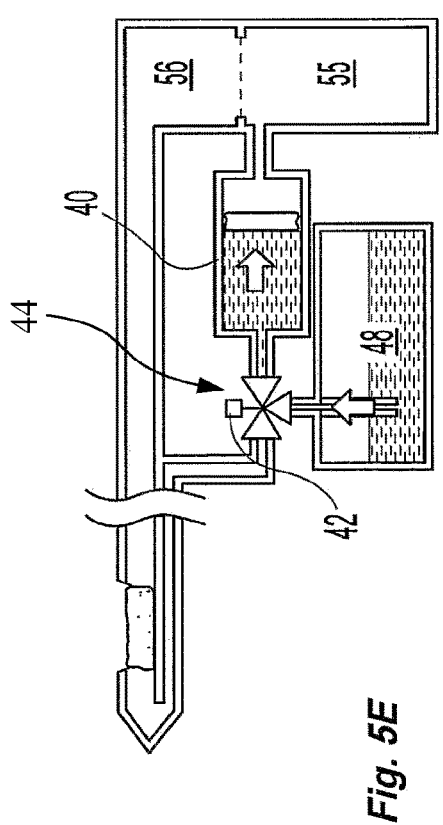
Figure 5F:
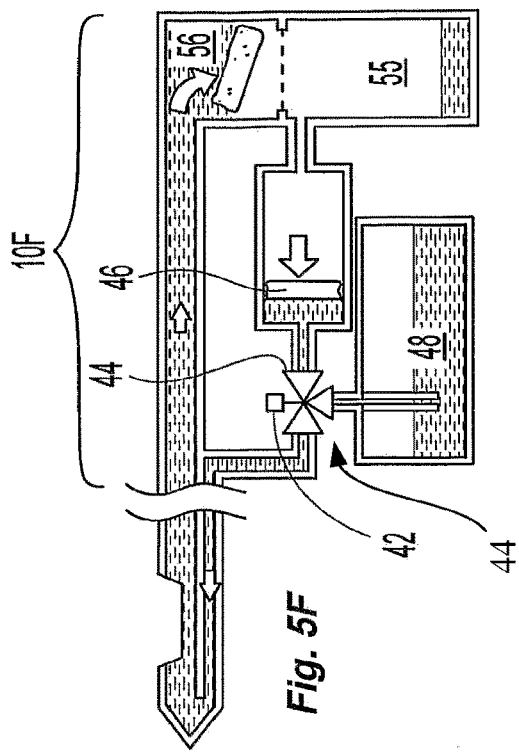
Figure 5G:
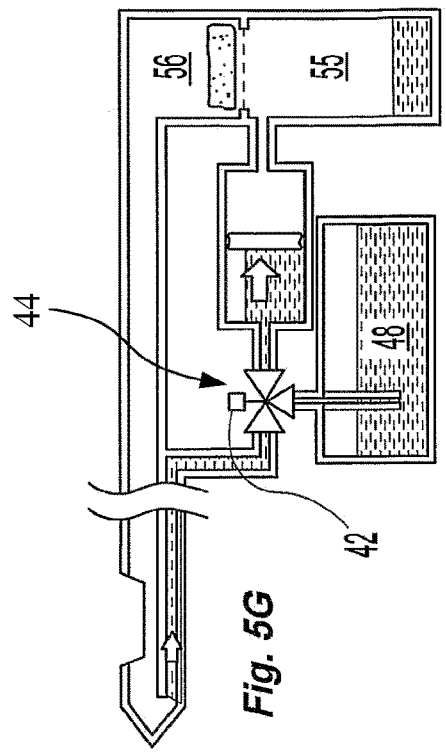
Figure 5H:
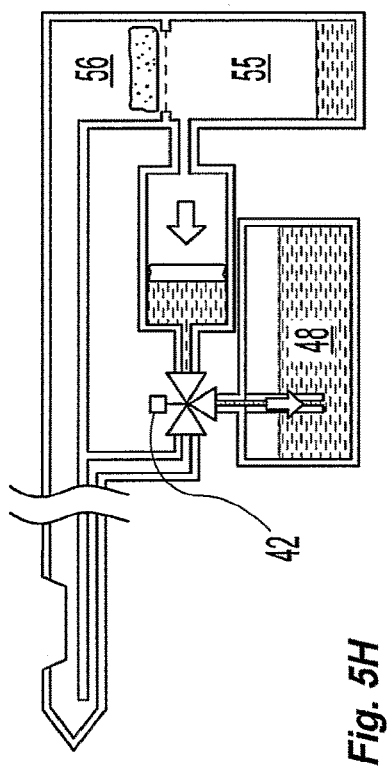

At this point, shown here in FIG. 5E, the four-way valve 44, with a vent 42 at one branch, is configured to allow the dual-action pump 40 to draw saline into port 40B. With the outer cannula 20 covering the port 10A (not shown for clarity), the dual-action pump 40, via the four-way valve 44, forces saline to flow through passage 10B, causing the tissue sample to be transported proximally towards through-port 20A (FIG. 5F). As the sample encounters the mesh material 39B in a collection vial or cartridge, it remains in place while residual saline falls into the sump 55. Any remaining saline in the lumens can be drawn back into the reservoir 48 by first drawing from the lumens into the chamber 45 (FIG. 5G) and then pumping into the reservoir 48 (FIG. 5H) for subsequent use by the dual-action pump 40.

Figure 5J:
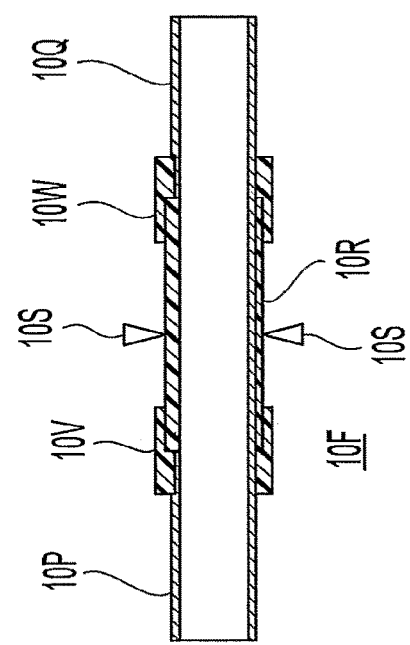

Referring to FIG. 5J, in an alternative embodiment, the passage 10F is provided with a flexible tube segment 10R that can be pinch-clamped by means of a valve actuator 10S. In this configuration, a pair of inline connectors 10V and 10W provides a smooth transition from a lead in part 10P to a lead out part 10Q to allow fluid and samples to pass through as in the earlier embodiment of passage 10F. The reason for adding this capability to close the valve is to allow a stronger vacuum to be developed in the sample area 10A by improving the volumetric efficiency of the dual action pump 40. To apply a vacuum to sample port 10A, the piston valve is configured as illustrated in FIG. 5F. However, unlike the situation in FIG. 5E, in this case, there is fluid only in the sump 48 as depicted in FIG. 5D. The clamp 10S is closed. The piston 46 is moved to the right to generate the vacuum by expanding the volume of chamber 45. Because the passage 10P is closed, the total volume evacuated, relative to the chamber volume 45, is markedly decreased. This configuration of passage 10P also has the advantage of avoiding the need for vacuum-competent sealing of the collection chamber 56 and sump 55.

FIGS. 6A1-6A3 illustrate a rotary-to-linear type tissue transport assembly 57 utilizing a shuttle 10. In this embodiment, the shuttle 34 is coupled to a helically threaded member via a suitable joint coupling. The joint coupling allows the shuttle to remain in a generally fixed orientation (e.g., upwardly oriented) while an inner cannula 21 with external threads are rotated against the stylet 10 (provided with internal threads), which allows the inner cannula 21 to convert the rotary motion of the cannula 21 into a linear motion while the stylet 10 remains stationary. The number and nature of the internal threads can be designed to achieve a sufficient transport speed with little or no back drive or backlash in the system. A fixed elongate slide 34B passing through and engaged in a slot 34A in the shuttle 34 may be used to prevent the shuttle 34 from rotating while permitting it to travel along the cannula 20. An outer cannula 20 can be used to sever the tissue sample from its main mass. Alternatively, a cannula disposed internally of the stylet 10 can also be used. Thereafter, the internal cannula 21 is rotated against the internal threads of the stylet 10 to transport the shuttle 34 to a tissue ejection port 20A.

FIGS. 6B1-6B3 illustrate a linear motion by longitudinal expansion of a plurality of nested elongated members. The shuttle 34 is connected to a first elongated member 21A that is nestable to second elongated member 21B, that is nestable to a third elongated member 21C and so on. The shuttle 34 and nested elongated members are disposed inside the stylet 10 (not shown for clarity). There may be any desired number of nested members such as 21A through 21C. Further, any of a variety of linear actuator devices may be employed. As in the embodiment of FIGS. 6A1-6A4, a fixed elongate slide 34B passing through and engaged in a slot 34A in the shuttle 34 may be used to prevent the shuttle 34 from rotating while permitting it to travel along the cannula 20. Each of the nested members may be provided with a stop so that when it reaches the end of a permitted range of travel relative to the member in which it is inserted, it is prevented from rotating further. In this way, only the most proximal member (e.g., 21C) needs to be rotated to extend and retract the shuttle 34.

As is the case above, the outer cannula 20 can be used to sever the tissue sample from its main mass. Alternatively, a cannula disposed internally of the stylet 10 can also be used. With the tissue contained in the shuttle 34, a suitable mechanism can be used to translate the shuttle in a linear motion between the first port 10A and second port 20A. For example, a Bowden type cable can be connected to the first elongated member through the interior of the second and third elongated members so that one to one movement of the cable would force the first elongated member 21A to telescope out of the interior of the second elongated member 21B. Further expansion of the cable would force the second elongated member 21B to telescope out of the interior of the third elongated member 21C (FIG. 6B2). Retraction of the cable would force the member to be nested inside each other in proximal direction (FIG. 6B3). Alternatively, a hydraulic mechanism can be used to telescopically expand these members by pressurizing the interiors of the elongated members 21B and 21C with a suitable bio-compatible liquid. Retraction of the members 21A, 21B, and 21C into a nested configuration can be achieved by providing a vacuum that extracts the liquid out of the interiors of the elongated members. Orifices 34A can be formed in the underside of shuttle 34 (e.g., FIGS. 4A and 4C) so that vacuum can be provided for siphoning of tissue at port 10A and ejection of the tissue by pressurized fluid at port 20A into a tissue vial or cartridge. Alternatively, a mechanical ejector 34B can also be used.

Each of the above embodiments can be utilized with a suitably sized stylet. For a 14 gauge stylet or needle, the internal volume is sufficient to capture a mass of at least 150 milligrams of biological tissues, e.g., turkey breast tissues. For a 10 gauge stylet 10, the internal volume is sufficient to capture a mass of at least 50 milligrams or more of biological tissues, e.g., turkey breast tissues. The length of the stylet 10 can be of any suitable lengths, such as, for example, about 250 to about 300 millimeters. The volume V of the housing containing all of the components of the device 100 is preferably 500 cubic centimeters or less and preferably about 320 cubic centimeters with particularly preferable dimensions of about 40 millimeters by about 40 millimeters and about 200 millimeters. As used herein, the term "about" or "approximately" for any numerical values indicates a suitable dimensional tolerance that allows the part or collection of components to function for its intended purpose as a biopsy cutter, biopsy system or the combination of both the system and cutter.

The cutting action by the cannula 20 can be by translation, rotation, translation and rotation or a combination of these movements along with back and forth axial movements of the cannula 20 as part of the cutting strategy. In the preferred embodiments, the drive unit can be a suitable drive unit such as the one shown and described, by way of example, in FIGS. 2, 9A, and 10A of U.S. Patent Application Publication No. 2005/0165328 published on Jul. 28, 2005, which publication is incorporated by reference in its entirety into this application.

The examples shown in the illustrations and described in detail above can be integrated with one or more of four exemplary marking systems. In particular, each of four marking systems can be integrated with each of the examples described above to provide for at least 32 different integrated biopsy cutter and marker systems. For clarity, only the four marking systems will be described and shown below. However, those skilled in the art can combine each marker system with each of the biopsy cutter systems as appropriate to arrive at a suitable permutation of biopsy sampling device and integrated marker.

Referring to FIGS. 7A-7G, a marker system utilizing a hook type marker 50 (i.e., a "harpoon") to prevent migration of the marker 50 once it has been deployed, is shown. The hook type marker 50 with hook 52 can be deployed in sequence or simultaneously with the sampling of biopsy tissues with the various technologies described in relation to FIGS. 1-6 above. As shown in FIGS. 7A and 7E, a member (e.g., an internal D-Rod 14A, 14B, or the outer cannula 20) can be used to eject a marker 50 stored in the stylet tip 11. In the exemplary embodiment of FIGS. 7A-7G, a second tracer 14B is provided with a cut-out portion 14B1 having a ramp 14B2 formed on a distal end of the rod 14B. The ramp 14B2 can be used (depending on whether the cannula 20 or rod 14B is axially translated only, rotated only or a combination of axial translation and rotation) to ensure that the marker 50 is deposited sufficiently near the tissue sampling site. Various marker configurations can be utilized. For example, as shown in FIG. 7D, a marker with wire like hooks 50A, square sectioned hook 50B, or marker with serrated edges 50C can be used in this system.

Figure 8B:
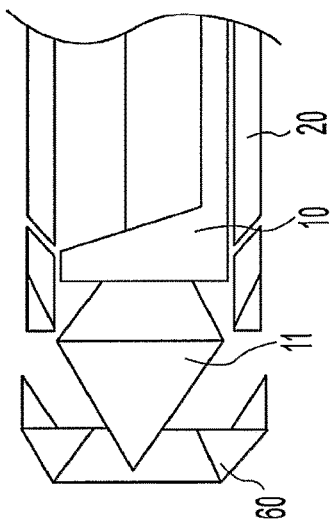
FIGS. 8A-8D illustrate another integrated biopsy marker system for the transport assembly of FIGS. 1-6.
Figure 8D:
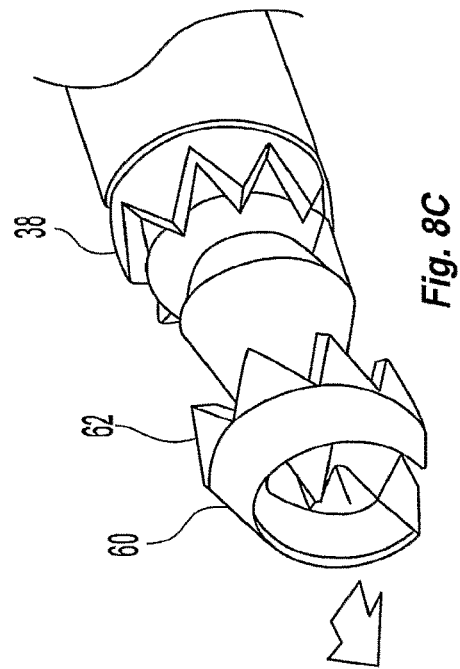
Figure 8A:
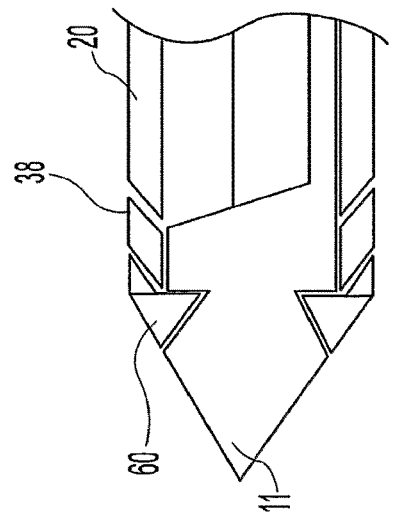
Figure 8C:
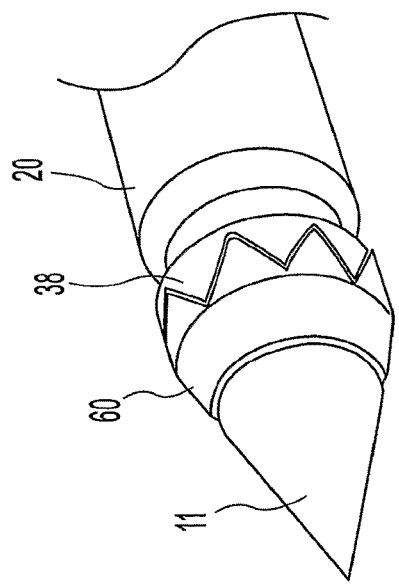

Referring to FIGS. 8A-8D, a marker system utilizing a split ring marker 60 can be utilized with various biopsy techniques described above in relation to FIGS. 1-5. In FIG. 8A, the split-ring marker 60 can be mounted to the stylet 10 via a suitable technique such as, for example, crimping, swaging or semi-permanent bonding. Optionally, an intermediate member 38 that forms a seal with the cannula or cutter 20 can be provided to maintain a generally constant outer diameter of the cannula 20 without an abrupt transition to the tip 11. The split-ring marker 60 can be deployed by itself, simultaneously with the sampling of the tissue, prior to sampling or subsequent to the sampling. As shown in FIG. 8B, the stylet tip 11 can be actuated proximally towards the user to force the split-ring marker 60 to detach from the tip 11. Alternatively, the outer cannula 20 can be actuated distally away from the user to force the split-ring marker 60 to separate from the stylet tip 11.

Referring to FIGS. 9A1, 9A2, 9A3, 9B and 9C, a marker system using a blossom-type marker 70 can be utilized with various biopsy techniques described above in relation to FIGS. 1 and 2. As shown in FIGS. 9A1 and 9B, the blossom marker 70 is mounted on a specially configured stylet tip 110 (see also FIG. 9C), which has grooves 112 and ramps 114 disposed about a longitudinal axis of the tip 110. The blossom marker 70 can be mounted by a suitable technique, such as, for example, crimping, swaging, or casting onto the specially configured stylet tip 110. As shown in FIGS. 9A1, 9A2 and 9B, the outer cannula 20 can be moved distally away from the user to force the blossom marker to be separated from the stylet tip 110. As the marker 70 is separated from the tip 110 (see FIGS. 9A3 and 9C), the ramps 114 on the tip 110 force the sectioned tips 72A-72E to blossom radially, thereby forming hooks 74A-74E. Alternatively, the stylet tip 110 can be actuated proximally towards the user so that the marker is deployed via contact against the outer cannula 20.

Referring to FIGS. 10A and 10B, another marker system is shown which uses a spiral-type marker 80 in conjunction with various biopsy systems described above in relation to FIGS. 1-6. As shown in FIG. 10A, a coiled marker wire 80 can be disposed in a hollowed out section 110 of the stylet tip 11. A suitable deployment mechanism can be used to eject the coiled marker wire out of its storage space in the stylet tip 11. The deployment mechanism can be a suitable mechanism, such as, for example, a linear-to-rotary motion converter that converts a linear motion into a rotary motion to rotatably expel the marker.

The materials suitable for use as part of each marker can be, for example, stainless steel, gold, titanium, platinum, tantalum, barium sulfate, biodegradable iron or shape memory polymer or metal alloy such as Nitinol. It is noted that Nitinol is radio-opaque, ultrasonically opaque and MRI compatible and therefore would be preferred by itself or in combination with other materials described herein and as known to those skilled in the art. Further, the markers can be of any suitable size so that it can be fitted onto a 7, 8, 9, 10, 11, 12, 14, or 16 gauge needle.

Although the markers have been shown as a single deployment marker, some of the embodiments disclosed herein can be utilized in a multiple deployment aspect. For example, the tip 11 can be configured to store a plurality of harpoon markers 50; the stylet 10 can be mounted with a longitudinal series of split-ring markers 60; the tip 11 can be configured with a cutter so that multiple helical markers 80 can be deployed.

Moreover, while specific embodiments have been described, various combinations of components and features can be obtained. For example, the paddle transport of FIGS. 1A-1D can be utilized with the threaded transport of FIGS. 6A1-6A3 by forming threads on the paddle connectors 18A, 16A, 14A, and 12A. The roller transport of FIGS. 2A-2E can be utilized for the paddle connectors of FIGS. 1A-1D. The bandolier type cartridges 39 of FIG. 5C can be utilized for any of the transport subassemblies described herein. The hydraulic and vacuum transport system of FIGS. 5D-5G can be utilized in any one of the embodiments described herein. Thus, it is clear to one skilled in the art that various permutations of components, sub-components and features can be utilized with the embodiments described herein and each seven transport devices is not limited only to the specific embodiment described herein.

Referring to FIG. 11, in all of the above embodiments, various motors, drives, valves, and other actuators are variously described along with their respective operations and operational sequences. It is clear from the particulars of each embodiment that a device may employ a controller 350 such as a programmable microprocessor controller, to provide the described functionality.

While the present invention has been disclosed with reference to certain preferred embodiments, numerous modifications, alterations, and changes to the described embodiments are possible without departing from the sphere and scope of the present invention, which is described, by way of example, above. Accordingly, it is intended that the present invention not be limited to the described embodiments, but that it have the full scope and equivalents thereof.

The invention claimed is:

1. A biopsy device comprising:
  a biopsy sample extraction needle with a sample extraction end, a recovery end, and a transport channel linking the sample extraction and recovery ends;
  a pump;
  a multi-way valve in fluid communication with the biopsy sample extraction needle and the pump wherein the multi-way valve has a plurality of positions; and
  a fluid reservoir configured to contain a fluid, the fluid reservoir being in fluid communication with the transport channel and the pump,
  the pump and the multi-way valve configured to switch between multiple system configurations, including:
    a first configuration wherein the multi-way valve has a first position that directly connects the pump to an ambient vent and the pump can reduce the pressure in at least the sample extraction end of the biopsy sample extraction needle;
    a second configuration wherein the multi-way valve has a second position that directly connects the pump to the fluid reservoir and the pump can draw the fluid from the fluid reservoir; and
    a third configuration wherein the multi-way valve has a third position that directly connects the pump to the sample extraction end of the biopsy sample extraction needle and the pump can supply the fluid to the sample extraction end to flush the fluid along the transport channel from the sample extraction end to the recovery end in a manner capable of transporting a sample along the transport channel, wherein in the third configuration the pump is also configured to simultaneously pull a vacuum on the recovery end while supplying the fluid to the sample extraction end.

2. The device of claim 1 further comprising a fourth system configuration wherein the multi-way valve has the third position and the pump can flush air along the transport channel from the recovery end to the sample extraction end.

3. The device of claim 2 wherein the pump comprises a first port connected to the multi-way valve and a second port connected to the recovery end.

4. The device of claim 3 further comprising a sump in fluid communication with the second port and with the recovery end.

5. The device of claim 2 further comprising a fifth system configuration wherein the multi-way valve has the second position and the pump is configured to pump fluid from a first port of the pump into the reservoir.

6. The device of claim 5 wherein the pump comprises the first port connected to the unitary multi-way valve and a second port connected to the recovery end.

7. The device of claim 6 further comprising a sump in fluid communication with the second port and with the recovery end.

8. The device of claim 5 further comprising a sump in fluid communication with the pump and with the recovery end.

9. The device of claim 1 wherein the pump comprises a first port connected to the multi-way valve and a second port connected to the recovery end.

10. The device of claim 9 further comprising a sump in fluid communication with the second port and with the recovery end.

11. The device of claim 9 wherein the second position and the third position are not the same.

12. The device of claim 1 wherein the second position and the third position are not the same.

13. The device of claim 12 further comprising a fourth system configuration wherein the multi-way valve has the third position and the pump can flush air along the transport channel from the recovery end to the sample extraction end.

14. The device of claim 13 wherein the pump comprises a first port connected to the multi-way valve and a second port connected to the recovery end.

15. The device of claim 14 further comprising a sump in fluid communication with the second port and with the recovery end.

* * * * *